United States Patent [19]
Cheng et al.

[11] Patent Number: 6,100,240
[45] Date of Patent: Aug. 8, 2000

[54] MACROLIDE DERIVATIVES

[75] Inventors: Hengmiao Cheng, East Lyme; Robert John Rafka, Stonington; Jason K. Dutra, Salem; Michael A. Letavic, Mystic; Brian S. Bronk, Gales Ferry, all of Conn.

[73] Assignee: Pfizer Inc, New York, N.Y.

[21] Appl. No.: 09/396,876

[22] Filed: Sep. 16, 1999

Related U.S. Application Data

[60] Provisional application No. 60/103,838, Oct. 9, 1998.
[51] Int. Cl.[7] ............................ A61K 31/70; C07H 17/08
[52] U.S. Cl. ................ 514/29; 536/7.2; 536/7.4; 536/18.5
[58] Field of Search ................... 536/7.2, 7.4, 18.5; 514/29

[56] References Cited

U.S. PATENT DOCUMENTS 5,641,753   6/1997   Platt ........................................ 514/29

*Primary Examiner*—Elli Peselev
*Attorney, Agent, or Firm*—Peter C. Richardson; Paul H. Ginsburg

[57] ABSTRACT

The invention relates to compounds of the formula I

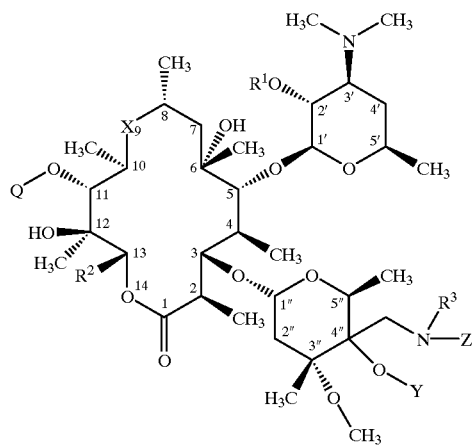

and to pharmaceutically acceptable salts thereof, wherein $R^1$, $R^2$, $R^3$, Q, X, Y and Z are as defined herein. The invention also relates to pharmaceutical compositions containing the compounds of formula I, methods of using said compounds of formula I in the treatment of infections, and methods of preparing said compounds of formula I.

68 Claims, No Drawings

MACROLIDE DERIVATIVES

This application claims benefit of Provisional Application 60/103,838, filed Oct. 9, 1998.

BACKGROUND OF THE INVENTION

This invention relates to novel 4" and 11-modified macrolides that are useful as antibacterial agents and antiprotozoa agents and other applications (e.g., anticancer, atherosclerosis, gastric motility reduction, etc.) in mammals, including man, as well as in fish and birds. This invention also relates to pharmaceutical compositions containing the novel compounds and to methods of treating bacterial infections and protozoa infections and in mammals, fish and birds by administering the novel compounds to mammals, fish and birds requiring such treatment.

Macrolide antibiotics are known to be useful in the treatment of a broad spectrum of bacterial infections and protozoa infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Additional macrolides are referred to in U.S. patent application Ser. No. 60/063,676, filed Oct. 29, 1997 (Yong-Jin Wu), U.S. application Ser. No. 60/063,161, filed Oct. 29, 1997 (Yong-Jin Wu), U.S. application Ser. No. 60/054,866, filed Aug. 6, 1997(Hiroko Masamune, Yong-Jin Wu, Takushi Kaneko and Paul R. McGuirk), U.S. application Ser. No. 60/049,980, filed Jun. 11, 1997 (Brian S. Bronk, Henry Cheng, E. A. Glaser, Michael A. Letavic, Takushi Kaneko and Bingwei V. Yang), U.S. application Ser. No. 60/049,348, filed Jun. 11, 1997 (Brian S. Bronk, Henry Cheng, E. A. Glaser, Michael A. Letavic, Takushi Kaneko and Bingwei V. Yang), International Application No. PCT/GB97/01810 filed Jul. 4, 1997 (Peter Francis Leadlay, James Staunton, Jesus Cortes and Michael Stephen Pacey), International Application No. PCT/GB97/01819 filed Jul. 4, 1997 (Peter Francis Leadlay, James Staunton, and Jesus Cortes), U.S. application Ser. No. 60/070,343, filed Jan. 2, 1998 (Dirlam), U.S. application Ser. No. 60/070,358, filed Jan. 2, 1998 (Yong-Jin Wu) and U.S. application Ser. No. 60/097,075, filed Aug. 19, 1998 (Hengmiao Cheng, Michael A. Letavic, Carl B. Ziegler, Jason K. Dutra, Peter Bertinato, Brian S. Bronk), all of which are incorporated herein by reference in their entirety. Like azithromycin and other macrolide antibiotics, the novel macrolide compounds of the present invention possess potent activity against various bacterial infections and protozoa infections as described below.

SUMMARY OF THE INVENTION

The present invention relates to compounds of the formula I

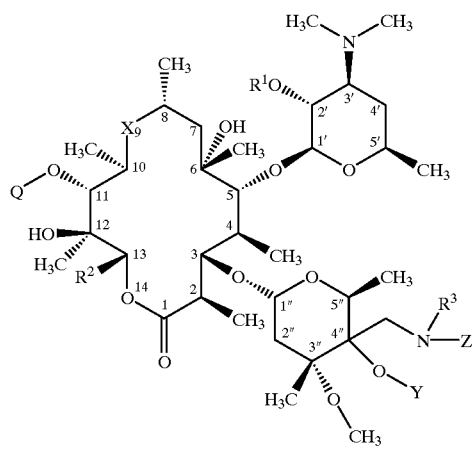

or a pharmaceutically acceptable salt thereof, wherein:

X is —$CH_2NR^4$— or —$NR^4CH_2$— wherein the first dash of each of the foregoing X groups is attached to the C-10 carbon of the compound of formula I and the last dash of each group is attached to the C-8 carbon of the compound of formula I;

Q is H or is a compound of the formula

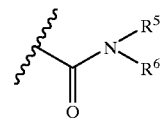

Y is H;

Z is —$C(=O)R^7$, —$S(=O)_nR^{10}$, or —$C(=O)OR^{10}$ wherein n is an integer ranging from 1 to 2;

$R^1$ is H or a hydroxy protecting group;

$R^2$ is an alpha-branched $C_2$–$C_8$ alkyl, alkenyl, alkynyl, alkoxyalkyl or alkylthioalkyl group, any of which may optionally be substituted by one or more hydroxyl groups, a $C_5$–$C_8$ cycloalkylalkyl group wherein the alkyl group is an alpha-branched $C_2$–$C_5$ alkyl group, a $C_3$–$C_8$ cycloalkyl or a $C_5$–$C_8$ cycloalkenyl group, either of which may optionally be substituted by methyl or one or more hydroxyl groups or one or more $C_1$–$C_4$ alkyl groups or halo atoms, or a 3 to 6 membered oxygen or sulphur containing heterocyclic ring which may be saturated, or fully or partially unsaturated, and which may optionally be substituted by one or more $C_1$–$C_4$ alkyl groups or halo atoms;

or $R^2$ is phenyl, which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl and cyano;

$R^3$ is H, $C_1$–$C_{10}$ alkyl, $C_2$–$C_{10}$-alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^3$ groups are optionally substituted by 1 to 3 substituents independently selected from halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl and a 5–10 membered heteroaryl;

$R^4$ is H, $C_1$–$C_{10}$ alkyl, $C_2$–$C_{10}$ alkenyl, $C_2$–$C_{10}$ alkynyl, —$(CH_2)_mC_6$–$C_{10}$aryl, or —$(CH_2)_m$(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

each $R^5$ and $R^6$ is independently H, $C_1$–$C_{10}$ alkyl, $C_2$–$C_{10}$ alkenyl, $C_2$–$C_{10}$ alkynyl, —(CH$_2$)$_m$$C_6$–$C_{10}$ aryl, or —(CH$_2$)$_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

or $R^5$ and $R^6$ may be taken together to form a 4–7 membered saturated ring or a 5–10 membered heteroaryl ring, wherein said saturated and heteroaryl rings optionally include 1 or 2 heteroatoms selected from O, S, and N, in addition to the nitrogen to which $R^5$ and $R^6$ are attached, wherein said saturated ring optionally includes 1 or 2 carbon-carbon double or triple bonds, and said saturated and heteroaryl rings are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

$R^7$ is $C_1$–$C_{10}$ alkyl, $C_2$–$C_{10}$ alkenyl, $C_2$–$C_{10}$ alkynyl, —CH$_2$O$R^8$, —CH$_2$$NR^8R^9$, —(CH$_2$)$_m$($C_6$–$C_{10}$ aryl), or —(CH$_2$)$_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

each $R^8$ and $R^9$ is independently H, hydroxy, $C_1$–$C_6$ alkoxy, $C_1$–$C_6$ alkyl, $C_2$–$C_6$ alkenyl, (CH$_2$)$_m$($C_6$–$C_{10}$ aryl), (CH$_2$)$_m$(5–10 membered heteroaryl), wherein m is an integer ranging from 0 to 4, or $C_2$–$C_{10}$ alkylyl;

$R^{10}$ is $C_1$–$C_{10}$ alkyl, $C_2$–$C_{10}$ alkenyl, $C_2$–$C_{10}$ alkynyl, —(CH$_2$)$_m$($C_6$–$C_{10}$ aryl), or —(CH$_2$)$_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

or $R^3$ is absent and Y and Z are taken together to form a heterocyclic ring of the formula

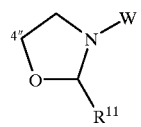

wherein W is H, —C(=O)$R^7$, —S(=O)$_n$$R^{10}$, —C(=O)O$R^{10}$, or —CH$_2$$R^7$ wherein n is an integer ranging from 1 to 2; and $R^{11}$ is H, $C_1$–$C_{10}$ alkyl, $C_2$–$C_{10}$ alkenyl, $C_2$–$C_{10}$ alkynyl, —(CH$_2$)$_m$$C_6$–$C_{10}$aryl, or —(CH$_2$)$_m$(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl.

Specific embodiments of this invention include the compounds of formula I wherein X is —$NR^4$CH$_2$— and more specifically, wherein $R^4$ is H or $C_1$–$C_{10}$ alkyl. More specific embodiments include those wherein $R^4$ is methyl, ethyl, propyl, butyl, cyclopropylmethyl, or cyclobutyl;

Other specific embodiments of this invention include the compound of formula I wherein X is —CH$_2$$NR^4$—. More specific embodiments include those wherein $R^4$ is H or $C_1$–$C_{10}$ alkyl. More specific embodiments include those wherein $R^4$ is methyl, ethyl, propyl, butyl, cyclopropylmethyl, or cyclobutyl.

Still other specific embodiments of this invention include the compounds of formula I wherein $R^3$ is H, $C_1$–$C_{10}$ alkyl, $C_2$–$C_{10}$-alkenyl, $C_2$–$C_{10}$ alkynyl, —(CH$_2$)$_m$($C_6$–$C_{10}$ aryl), or —(CH$_2$)$_m$(5–10 membered heteroaryl), wherein m is an integer ranging from 0 to 4, and wherein the alkyl, alkenyl, alkynyl, aryl and heteroaryl moieties of the foregoing $R^3$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl and a 5–10 membered heteroaryl. More specific embodiments of this invention include those compounds wherein $R^3$ is H or $C_1$–$C_{10}$ alkyl.

Other specific embodiments of this invention include the compounds of formula I wherein $R^3$ is absent and Y and Z are taken together to form a heterocyclic ring of the formula

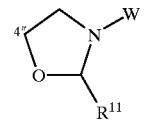

wherein W is H, —C(=O)$R^7$, —S(=O)$_n$$R^{10}$O, —C(=O)O$R^{10}$, or —CH$_2$$R^7$ wherein n is an integer ranging from 1 to 2. More specific embodiments of this invention include those compounds wherein W is H.

Other specific embodiments of this invention include the compounds of formula I wherein Z is —C(=O)$R^7$.

More specific embodiments of this invention include those compounds $R^7$ is $C_1$–$C_{10}$ alkyl.

Other specific embodiments of this invention include the compounds of formula I wherein Z is —S(=O)$_n$$R^{10}$ or Z is —C(=O)O$R^{10}$. More specific embodiments of this invention include those compounds wherein $R^{10}$ is $C_1$–$C_{10}$ alkyl.

Still other specific embodiments of this invention include the compounds of formula I wherein Q is H.

Still other specific embodiments of this invention include the compounds of formula I wherein Q is a compound of the formula

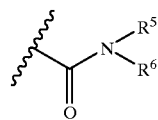

More specific embodiments of this invention include those compounds wherein each $R^5$ and $R^6$ is independently H, $C_1$–$C_{10}$ alkyl, $C_2$–$C_{10}$ alkenyl, $C_2$–$C_{10}$ alkynyl, —$(CH_2)_m C_6$–$C_{10}$ aryl, or —$(CH_2)_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl. Other more specific embodiments of this invention include those compounds wherein $R^5$ and $R^6$ may be taken together to form a 4–7 membered saturated ring or a 5–10 membered heteroaryl ring, wherein said saturated and heteroaryl rings optionally include 1 or 2 heteroatoms selected from O, S, and N, in addition to the nitrogen to which $R^5$ and $R^6$ are attached, wherein said saturated ring optionally includes 1 or 2 carbon-carbon double or triple bonds, and said saturated and heteroaryl rings are optionally substituted by 1 to 3 substituents independently selected from halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl.

Other specific embodiments of this invention include the compounds of formula I wherein $R^2$ is an alpha-branched $C_2$–$C_8$ alkyl, alkenyl, alkynyl, alkoxyalkyl or alkylthioalkyl group, any of which may optionally be substituted by one or more hydroxyl groups, a $C_5$–$C_8$ cycloalkylalkyl group wherein the alkyl group is an alpha-branched $C_2$–$C_5$ alkyl group, a $C_3$–$C_8$ cycloalkyl or a $C_5$–$C_8$ cycloalkenyl group, either of which may optionally be substituted by methyl or one or more hydroxyl groups or one or more $C_1$–$C_4$ alkyl groups or halo atoms, or a 3 to 6 membered oxygen or sulphur containing heterocyclic ring which may be saturated, or fully or partially unsaturated, and which may optionally be substituted by one or more $C_1$–$C_4$ alkyl groups or halo atoms. More specific embodiments of this invention include those compounds wherein $R^2$ is an alpha-branched $C_2$–$C_8$ alkyl. Still more specific embodiments of this invention include those compounds wherein $R^2$ is ethyl.

Other specific embodiments of this invention include the compounds of formula I wherein $R^2$ is phenyl, which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl and cyano.

Other specific embodiments of this invention include the compounds of formula I wherein $R^1$ is H.

Specific embodiments of this invention include compounds of formula I wherein Q is H;

$R^1$ is H;
$R^2$ is ethyl;
$R^3$ is H or $C_1$–$C_{10}$ alkyl;
$R^4$ is H, methyl, ethyl, propyl, butyl, cyclopropylmethyl, or cyclobutyl;
Y is H;
$R^7$ is $C_1$–$C_{10}$ alkyl, $C_2$–$C_{10}$ alkenyl, $C_2$–$C_{10}$ alkynyl, —$CH_2OR^8$, —$CH_2NR^8R^9$, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

$R^{10}$ is $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl; and the pharmaceutically acceptable salts of the foregoing compounds.

Other specific embodiments of this invention include compounds of formula I wherein Q is H;
$R^1$ is H;
$R^2$ is ethyl;
$R^4$ is H, methyl, ethyl, propyl, butyl, cyclopropylmethyl, or cyclobutyl; and
$R^3$ is absent and Y and Z are taken together to form a heterocyclic ring of the formula

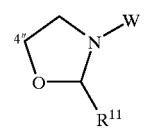

wherein $R^{11}$ is H and W is H, —C(=O)$R^7$, —S(=O)$_n R^{10}$, —C(=O)O$R^{10}$, or —$CH_2R^7$ wherein n is an integer ranging from 1 to 2;

$R^7$ is $C_1$–$C_{10}$ alkyl, $C_2$–$C_{10}$ alkenyl, $C_2$–$C_{10}$ alkynyl, —$CH_2OR^8$, —$CH_2NR^8R^9$, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

$R^{10}$ is $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl; and the pharmaceutically acceptable salts of the foregoing compounds.

Further specific embodiments of this invention include compounds of formula I wherein Q is a compound of the formula

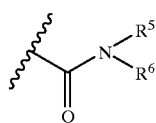

$R^1$ is H;
$R^2$ is ethyl;
$R^3$ is H or $C_1$–$C_{10}$ alkyl;
$R^4$ is H, methyl, ethyl, propyl, butyl, cyclopropylmethyl or cyclobutyl,
Y is H;
$R^5$ is H;
$R^6$ is $C_1$–$C_{10}$ alkyl, —$(CH_2)_m C_6$–$C_{10}$ aryl, or —$(CH_2)_m$ (5–10 membered heteroaryl), wherein m is an integer ranging from 0 to 4, and wherein the alkyl, aryl, heteroaryl moieties of the foregoing $R^6$ group is optionally substituted by 1 to 3 substituents independently selected from halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;
$R^7$ is $C_1$–$C_{10}$ alkyl, $C_2$–$C_{10}$ alkenyl, $C_2$–$C_{10}$ alkynyl, —$CH_2OR^8$, —$CH_2NR^8R^9$, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;
$R^{10}$ is $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl; and the pharmaceutically acceptable salts of the foregoing compounds.

Still further specific embodiments of this invention include compounds of formula I wherein
Q is a compound of the formula:

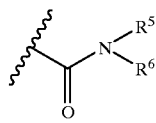

$R^1$ is H;
$R^2$ is ethyl;
$R^4$ is H, methyl, ethyl, propyl, butyl, cyclopropylmethyl, or cyclobutyl;
$R^5$ is H;
$R^6$ is $C_1$–$C_{10}$ alkyl, —$(CH_2)_m C_6$–$C_{10}$ aryl, or —$(CH_2)_m$ (5–10 membered heteroaryl), wherein m is an integer ranging from 0 to 4, and wherein the alkyl, aryl, heteroaryl moieties of the foregoing $R^6$ group is optionally substituted by 1 to 3 substituents independently selected from halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

and Y and Z are taken together to form a heterocyclic ring of the formula

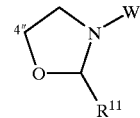

wherein $R^{11}$ is H and W is H, —C(=O)$R^7$, —S(=O)$_n R^{10}$, —C(=O)O$R^{10}$, or —$CH_2R^7$ wherein n is an integer ranging from 1 to 2;
$R^7$ is $C_1$–$C_{10}$ alkyl, $C_2$–$C_{10}$ alkenyl, $C_2$–$C_{10}$ alkynyl, —$CH_2OR^{10}$, —$CH_2NR^8R^9$, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;
$R^{10}$ is $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6 C_{10}$ aryl, and a 5–10 membered heteroaryl; and the pharmaceutically acceptable salts of the foregoing compounds.

Examples of preferred compounds of this invention include compounds of formula I wherein
Q is H;
$R^1$ is H;
$R^2$ is Et;
$R^3$ is H;
X is —$NR^4CH_2$—;
$R^4$ is $CH_3$;
Y is H;
Z is —C(=O)$R^7$; and
$R^7$ is selected from the group consisting of: 3-pyridyl, 2-furyl, 3-quinolinyl, 2-pyridyl, 4-pyridyl, 2-pyrazinyl, 4-acetamidophenyl, 2-pyrrole, 2-thiophene, 4-cinnolone and 7,8-difluoro-3-quinolinyl;
and the pharmaceutically acceptable salts of the foregoing compounds.

Other examples of preferred compounds of this invention include compounds of formula I wherein
Q is $R^6$NHC(=O)—;
$R^6$ is 3-pyridylmethyl;
$R^1$ is H;
$R^2$ is Et;
$R^3$ is H;
X is —$NR^4CH_2$—;
$R^4$ is $CH_3$;
Y is H;
Z is —C(=O)$R^7$; and
$R^7$ is selected from the group consisting of: 3-pyridyl, 2-furyl, 3-quinolinyl, 2-pyridyl, 4-pyridyl, 2-pyrazinyl, 4-acetamidophenyl, 2-pyrrole, 2-thiophene, 4-cinnolone and 7,8-difluoro-3-quinolinyl;
and the pharmaceutically acceptable salts of the foregoing compounds.

Still other examples of preferred compounds of this invention include compounds of formula I wherein R³ is absent and Y and Z are taken together to form a heterocyclic ring of the formula:

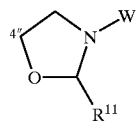

Q is H;
R¹ is H;
R² is Et;
X is —NR⁴CH₂—;
R⁴ is CH₃;
R¹¹ is H;
W is —C(=O)R⁷;
R⁷ is selected from the group consisting of: 3-pyridyl, 2-furyl, 3-quinolinyl, 2-pyridyl, 4-pyridyl, 2-pyrazinyl; 4-acetamidophenyl, 2-pyrrole, 2-thiophene, 4-cinnolone and 7,8-difluoro-3-quinolinyl;
and the pharmaceutically acceptable salts of the foregoing compounds.

Yet other examples of preferred compounds of this invention include compounds of formula I wherein
R³ is absent and Y and Z are taken together to form a heterocyclic ring of the formula:

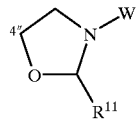

Q is H;
R¹ is H;
R² is Et;
X is —NR⁴CH₂—;
R⁴ is CH₃;
R¹¹ is H or Me;
W is ethyl, propyl or butyl;
and the pharmaceutically acceptable salts of the foregoing compounds.

Yet other examples of preferred compounds of this invention include compounds of formula I wherein
R³ is absent and Y and Z are taken together to form a heterocyclic ring of the formula:

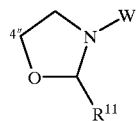

Q is R⁶NHC(=O)—;
R⁶ is 3-pyridylmethyl;
R¹ is H;
R² is Et;
X is —NR⁴CH₂—;
R⁴ is CH₃;
R¹¹ is H;
W is —C(=O)R⁷;
R⁷ is selected from the group consisting of: 3-pyridyl, 2-furyl, 3-quinolinyl, 2-pyridyl, 4-pyridyl, 2-pyrazinyl; 4-acetamidophenyl, 2-pyrrole, 2-thiophene, 4-cinnolone and 7,8-difluoro-3-quinolinyl;
and the pharmaceutically acceptable salts of the foregoing compounds.

The invention also relates to a pharmaceutical composition for the treatment of an infection in a mammal, fish or bird which comprises a therapeutically effective amount of a compound of formula I and a pharmaceutically acceptable carrier.

The invention also relates to a method of treating an infection in a mammal, fish, or bird which comprises administering to said mammal, fish, or bird a therapeutically effective amount of a compound of formula I.

The invention further relates to a compound of the formula II

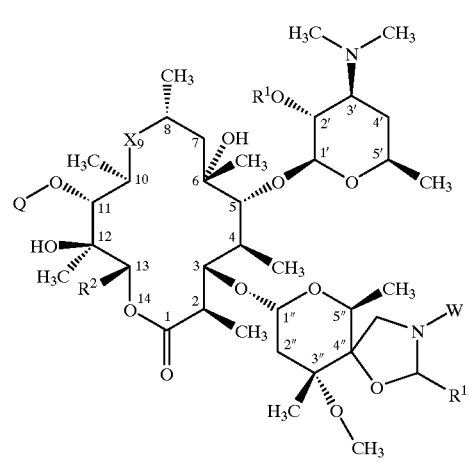

or a pharmaceutically acceptable salt thereof, wherein:
X is —CH₂NR⁴— or —NR⁴CH₂— wherein the first dash of each of the foregoing X groups is attached to C-10 carbon of the compound of formula II and the last dash of each group is attached to the C-8 carbon of the compound of formula II;
Q is H or is a compound of the formula

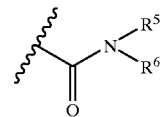

W is H, —C(=O)R⁷, —S(=O)ₙR¹⁰, —C(=O)OR¹⁰ or —CH₂R⁷ wherein n is an integer ranging from 1 to 2;
R¹ is H or a hydroxy protecting group;
R² is an alpha-branched C₂–C₈ alkyl, alkenyl, alkynyl, alkoxyalkyl or alkylthioalkyl group any of which may optionally be substituted by one or more hydroxyl groups, a C₅–C₈ cycloalkylalkyl group wherein the alkyl group is an alpha-branched C₂–C₅ alkyl group, a C₃–C₈ cycloalkyl or C₅–C₈ cycloalkenyl group, either of which may optionally be substituted by methyl or one or more hydroxyl or one or more C₁–C₄ alkyl groups or halo atoms, or a 3 to 6 membered oxygen or sulphur containing heterocyclic ring which may be saturated, or fully or partially unsaturated and which may optionally be substituted by one or more C₁–C₄ alkyl groups or halo atoms;
or R² is phenyl which may be optionally substituted with at least one substituent selected from C₁–C₄ alkyl, C₁–C₄ alkoxy and C₁–C₄ alkylthio groups, halogen atoms, hydroxyl groups, trifluoromethyl, and cyano;
R⁴ is H, C₁–C₁₀ alkyl, C₂–C₁₀ alkenyl, C₂–C₁₀ alkynyl, —(CH₂)ₘC₆–C₁₀aryl, —(CH₂)ₘ(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

each $R^5$ and $R^6$ is independently H, $C_1$–$C_{10}$ alkyl, $C_2$–$C_{10}$ alkenyl, $C_2$–$C_{10}$ alkynyl, —$(CH_2)_mC_6$–$C_{10}$ aryl, or —$(CH_2)_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

or $R^5$ and $R^6$ may be taken together to form a 4–7 membered saturated ring or a 5–10 membered heteroaryl ring, wherein said saturated and heteroaryl rings optionally include 1 or 2 heteroatoms selected from O, S, and N, in addition to the nitrogen to which $R^5$ and $R^6$ are attached, said saturated ring optionally includes 1 or 2 carbon-carbon double or triple bonds, and said saturated and heteroaryl rings are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

$R^7$ is $C_1$–$C_{10}$ alkyl, $C_2$–$C_{10}$-alkenyl, $C_2$–$C_{10}$ alkynyl, —$CH_2OR^8$, —$CH_2NR^8R^9$, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

each $R^8$ and $R^9$ is independently H, hydroxy, $C_1$–$C_6$ alkoxy, $C_1$–$C_6$ alkyl, $C_2$–$C_6$ alkenyl, $(CH_2)_m(C_6$–$C_{10}$ aryl), or $(CH_2)_m$(5–10 membered heteroaryl), wherein m is an integer ranging from 0 to 4, or $C_2$–$C_{10}$ alkylyl;

$R^{10}$ is $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from halo, cyano, nitro, trifluoromethyl, azido, —C(O)$R^8$, —OC(O)$R^8$, —$NR^8(O)R^9$, —C(O)$NR^8R^9$, —N $R^8R^9$, hydroxy, $C_1$–$C_6$ alkyl, $C_1$–$C_6$ alkoxy, $C_6$–$C_{10}$ aryl, and a 5–10 membered heteroaryl; and $R^{11}$ is H, $C_1$–$C_{10}$ alkyl, $C_2$–$C_{10}$ alkenyl, $C_2$–$C_{10}$ alkynyl, —$(CH_2)_mC_6$–$C_{10}$aryl, or —$(CH_2)_m$(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from halo, cyano, nitro, trifluoromethyl, azido, —C(O)$R^8$, —OC(O)$R^8$, —$NR^8(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl.

The present invention further relates to a compound according to formula II wherein Q is H;
$R^1$ is H;
$R^2$ is Et;
X is —$NR^4CH_2$—;
$R^4$ is $CH_3$;
$R^{11}$ is H;
W is —C(=O)$R^7$;
$R^7$ is selected from the group consisting of: 3-pyridyl, 2-furyl, 3-quinolinyl, 2-pyridyl, 4-pyridyl, 2-pyrazinyl, 4-acetamidophenyl, 2-pyrrole, 2-thiophene, 4-cinnolone and 7,8-difluoro-3-quinolinyl;

and the pharmaceutically acceptable salts of the foregoing compounds.

The invention also relates to a pharmaceutical composition for the treatment of an infection in a mammal, fish or bird which comprises a therapeutically effective amount of a compound of formula II and a pharmaceutically acceptable carrier.

The invention also relates to a method of treating an infection in a mammal, fish, or bird which comprises administering to said mammal, fish, or bird a therapeutically effective amount of a compound of formula II.

The invention also relates to a method of preparing a compound of the formula I

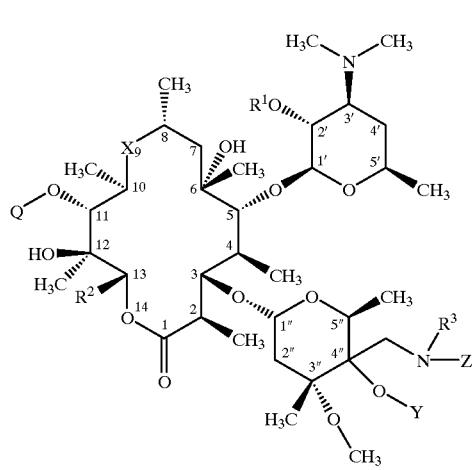

I or a pharmaceutically acceptable salt thereof, wherein:

X is —$CH_2NR^4$— or —$NR^4CH_2$— wherein the first dash of each of the fore going X groups is attached to the C-10 carbon of the compound of formula I and the last dash of each group is attached to the C-8 carbon of the compound of formula I;

Q is H or is a compound of the formula

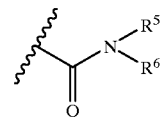

Y is H;
Z is —C(=O)$R^7$, —$S(=O)_nR^{10}$, or —$C(=O)_nR^{10}$ wherein n is an integer ranging from 1 to 2;
$R^1$ is H or a hydroxy protecting group;
$R^2$ is an alpha-branched $C_2$–$C_8$ alkyl, alkenyl, alkynyl, alkoxyalkyl or alkylthioalkyl group, any of which may optionally be substituted by one or more hydroxyl groups, a $C_5$–$C_8$ cycloalkylalkyl group wherein the alkyl group is an alpha-branched $C_2$–$C_5$ alkyl group, a $C_3$–$C_8$ cycloalkyl or a $C_5$–$C_8$ cycloalkenyl group, either of which may optionally be substituted by methyl or one or more hydroxyl groups or one or more $C_1$–$C_4$ alkyl groups or halo atoms, or a 3 to 6 membered oxygen or sulphur containing heterocyclic ring which may be saturated, or fully or partially unsaturated, and which may optionally be substituted by one or more $C_1$–$C_4$ alkyl groups or halo atoms;

or $R^2$ is phenyl, which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl and cyano;

$R^3$ is H, $C_1$–$C_{10}$ alkyl, $C_2$–$C_{10}$-alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^3$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl and a 5–10 membered heteroaryl;

$R^4$ is H, $C_1$–$C_{10}$ alkyl, $C_2$–$C_{10}$ alkenyl, $C_2$–$C_{10}$ alkynyl, —$(CH_2)_mC_6$–$C_{10}$aryl, or $(CH_2)_m$(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

each $R^5$ and $R^6$ is independently H, $C_1$–$C_{10}$ alkyl, $C_2$–$C_{10}$ alkenyl, $C_2$–$C_{10}$ alkynyl, —$(CH_2)_mC_6$–$C_{10}$ aryl, or —$(CH_2)_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_{10}$ alkoxy, $C_6$–$C_{10}$ aryl, and a 5–10 membered heteroaryl;

or $R^5$ and $R^6$ may be taken together to form a 4–7 membered saturated ring or a 5–10 membered heteroaryl ring, wherein said saturated and heteroaryl rings optionally include 1 or 2 heteroatoms selected from O, S, and N, in addition to the nitrogen to which $R^5$ and $R^6$ are attached, wherein said saturated ring optionally includes 1 or 2 carbon-carbon double or triple bonds, and said saturated and heteroaryl rings are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

$R^7$ is $C_1$–$C_{10}$ alkyl, $C_2$–$C_{10}$ alkenyl, $C_2$–$C_{10}$ alkynyl, —$CH_2OR^8$, —$CH_2NR^8R^9$, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

each $R^8$ and $R^9$ is independently H, hydroxy, $C_1$–$C_6$ alkoxy, $C_1$–$C_6$ alkyl, $C_2$–$C_6$ alkenyl, $(CH_2)_m(C_6$–$C_{10}$ aryl), $(CH_2)_m$(5–10 membered heteroaryl), wherein m is an integer ranging from 0 to 4, or $C_2$–$C_{10}$ alkylyl;

$R^{10}$ is $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

or $R^3$ is absent and Y and Z are taken together to form a heterocyclic ring of the formula

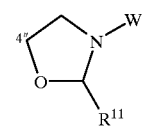

wherein W is H, —C(=O)$R^7$, —S(=O)$_nR^{10}$, —C(=O)O$R^{10}$, or —$CH_2R^7$ wherein n is an integer ranging from 1 to 2; and $R^{11}$ is H, $C_1$–$C_{10}$l alkyl, $C_2$–$C_{10}$ alkenyl, $C_2$–$C_{10}$ alkynyl, —$(CH_2)_mC_6$–$C_{10}$aryl, or —$(CH_2)_m$(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from halo, cyano, nitro, trifluoromethyl, azido, —C(O)$R^8$, —OC(O)$R^8$, —$NR^8C(O)R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl, which comprises treating a compound of the formula III

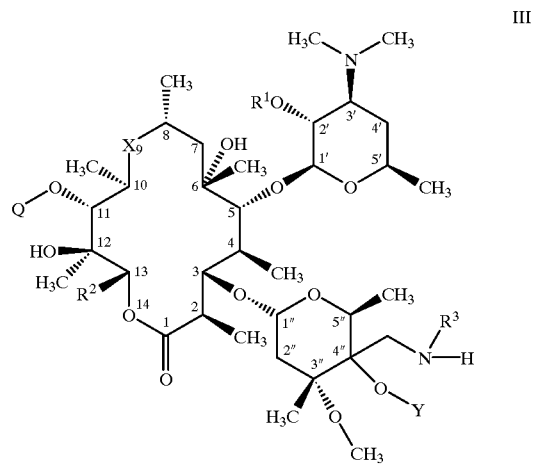

wherein Q, X, Y, $R^1$, $R^2$, $R^3$, $R^4$, $R^5$, $R^6$, $R^8$ and $R^9$ are as defined for the compound of formula I, with a compound of the formula $R^7C$(=O)OH or $R^{10}S$(=O)$_n$OH in the presence of a coupling reagent, or $R^{10}OC$(=O)Cl wherein n, $R^7$, $R^{10}$ are as defined for the compound of formula I. Examples of suitable coupling reagents include EDC (1-(3-Dimethylaminopropyl)-3-ethylcarbodiimide hydrochloride) and HOBt (1-Hydroxybenzotriazole).

The invention further relates to a method of preparing a compound of the formula II

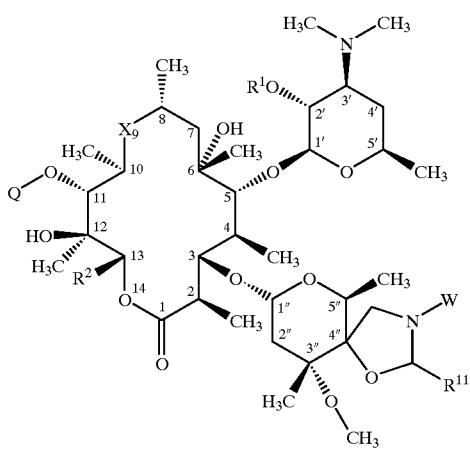

or a pharmaceutically acceptable salt thereof, wherein:

X is —$CH_2NR^4$— or —$NR^4CH_2$— wherein the first dash of each of the foregoing X groups is attached to C-10 carbon of the compound of formula II and the last dash of each group is attached to the C-8 carbon of the compound of formula II;

Q is H or is a compound of the formula

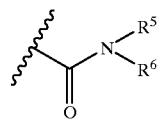

W is H, —$C(=O)R^7$, —$S(=O)_nR^{10}$, —$C(=O)OR^{10}$ or —$CH_2R^7$ wherein n is an integer ranging from 1 to 2;

$R^1$ is H or a hydroxy protecting group;

$R^2$ is an alpha-branched $C_2$–$C_8$ alkyl, alkenyl, alkynyl, alkoxyalkyl or alkylthioalkyl group any of which may optionally be substituted by one or more hydroxyl groups, a $C_5$–$C_8$ cycloalkylalkyl group wherein the alkyl group is an alpha-branched $C_2$–$C_5$ alkyl group, a $C_3$–$C_8$ cycloalkyl or $C_5$–$C_8$ cycloalkenyl group, either of which may optionally be substituted by methyl or one or more hydroxyl or one or more $C_1$–$C_4$ alkyl groups or halo atoms, or a 3 to 6 membered oxygen or sulphur containing heterocyclic ring which may be saturated, or fully or partially unsaturated and which may optionally be substituted by one or more $C_1$–$C_4$ alkyl groups or halo atoms;

or $R^2$ is phenyl which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl, and cyano;

$R^4$ is H, $C_1$–$C_{10}$ alkyl, $C_2$–$C_{10}$ alkenyl, $C_2$–$C_{10}$ alkynyl, —$(CH_2)_mC_6$–$C_{10}$aryl, —$(CH_2)_m$(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

each $R^5$ and $R^6$ is independently H, $C_1$–$C_{10}$ alkyl, $C_2$–$C_{10}$ alkenyl, $C_2$–$C_{10}$ alkynyl, —$(CH_2)_mC_6$–$C_{10}$ aryl, or —$(CH_2)_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C^6$ alkoxy, $C_6$–$C_{10}$ aryl, and a 5–10 membered heteroaryl;

or $R^5$ and $R^6$ may be taken together to form a 4–7 membered saturated ring or a 5–10 membered heteroaryl ring, wherein said saturated and heteroaryl rings optionally include 1 or 2 heteroatoms selected from O, S, and N, in addition to the nitrogen to which $R^5$ and $R^6$ are attached, said saturated ring optionally includes 1 or 2 carbon-carbon double or triple bonds, and said saturated and heteroaryl rings are optionally substituted by 1 to 3 substituents independently selected from halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_{10}$ alkoxy, $C_6$–$C_{10}$ aryl, and a 5–10 membered heteroaryl;

$R^7$ is $C_1$–$C_{10}$ alkyl, $C_2$–$C_{10}$-alkenyl, $C_2$–$C_{10}$ alkynyl, –$CH_2OR^8$, —$CH_2NR^8R^9$, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

each $R^8$ and $R^9$ is independently H, hydroxy, $C_1$–$C_6$ alkoxy, $C_1$–$C_6$ alkyl, $C_2$–$C_6$ alkenyl, $(CH_2)_m(C_6$–$C_{10}$ aryl), or $(CH_2)_m$(5–10 membered heteroaryl), wherein m is an integer ranging from 0 to 4, or $C_2$–$C_{10}$ alkylyl;

$R^{10}$ is $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from halo, cyano, nitro, trifluoromethyl, azido, —$C(O)R^8$, —$OC(O)R^8$, —$NR^8C(O)R$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl; and $R^{11}$ is H, $C_1$–$C_{10}$ alkyl, $C_2$–$C_{10}$ alkenyl, $C_2$–$C_{10}$ alkynyl, —$(CH_2)_mC_6$–$C_{10}$aryl, or —$(CH_2)_m$(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl, which comprises treating a compound of the formula IV

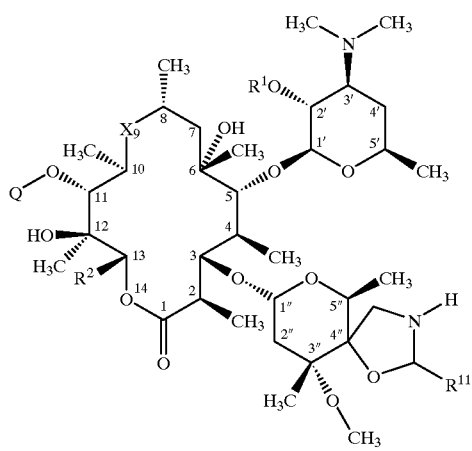

IV wherein Q, X, $R^1$, $R^2$, $R^4$, $R^5$, $R^6$, $R^8$, $R^9$, $R^{11}$ are as defined for the compound of formula II, with a compound of the formula $R^7C(=O)OH$ or $R^{10}OS(=O)_nOH$ in the presence of a coupling reagent, or $R^{10}OC(=O)Cl$, $R^7CHO$ in the presence of AcOH and $NaB(OAc)_3H$ wherein n, $R^7$, $R^{10}$ are as defined in the compound of formula II. Examples of suitable coupling reagents include EDC and HOBt.

The preparation of compounds of formula I or formula II wherein Q is —C(=O)$NR^5R^6$ can be prepared from compounds of formula I or formula II wherein Q is H by the method disclosed in U.S. patent application Ser. No. 60/097,075, filed Aug. 19, 1998 which is incorporated herein by reference in its entirety.

The compound of formula I wherein Q is H is prepared starting from compound 7. The 4"-epoxide of compound 7 is first opened by sodium azide in the presence of ammonium chloride in methanol/water to generate the azide derivative 8. The azide functional group in compound 8 is then converted to the corresponding amine derivative 9 by hydrogenation, and the resultant amine in compound 9 is coupled with a compound of the formula RC(=O)OH, RS(=O)$_2$OH in the presence of coupling reagents such as EDC and HOBt, or ROC(=O)Cl to give the compound of formula I wherein Q is H. The preparation of starting compounds 7 is described in U.S. patent application Ser. No. 60/049,348, filed Jun. 11, 1997, PCT/IB98/00839 (publication no. WO 98/56802), which is incorporated herein by reference in its entirety.

The compound of formula II wherein Q is H is also prepared starting from compound 9. When treated with an aldehyde in chloroform at elevated temperature, compound 9 is converted to 4"-oxozalidine derivative 13. The amino group in oxozalidine is then coupled with a compound of the formula RC(=O)OH, RS(=O)$_2$OH in the presence of coupling reagents such as EDC and HOBt, or ROC(=O)Cl, or RCHO in the presence of AcOH and $NaB(OAc)_3H$ to give the compound of formula II wherein Q is H.

The term "treatment", as used herein, unless otherwise indicated, includes the treatment or prevention of a bacterial infection or protozoa infection as provided in the method of the present invention.

Patients that can be treated with the compounds of formula I, and the pharmaceutically acceptable salts thereof, include mammals (particularly humans), fish, and birds suffering from infections caused by various microorganisms including Gram positive and Gram negative bacteria.

As used herein, unless otherwise indicated, the term "bacterial infection(s)" or "protozoa infections; includes bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or *Peptostreptococcus* spp.; pharynigitis, rheumatic fever, and glomerulonephritis related to infection by *Streptococcus pyogenes,* Groups C and G streptococci, *Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal groups C-F (minute-colony streptococci), viridans streptococci, *Corynebacterium minutissimum,* Clostridium spp., or *Bartonella henselae;* uncomplicated acute urinary tract infections related to infection by *Staphylococcus saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum,* or *Neiserria gonorrheae;* toxin diseases related to infection by *S. aureus* (food poisoning and Toxic shock syndrome), or Groups A, B, and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *Chlamydia trachomatis, Neisseria gonorrhoeae, S. aureus, S. pneumoniae, S. pyogenes, H. influenzae,* or Listeria spp.; disseminated *Mycobacterium avium* complex (MAC) disease related to infection by *Mycobacterium avium,* or *Mycobacterium intracellulare;* gastroenteritis related to infection by *Campylobacter jejuni;* intestinal protozoa related to infection by Cryptosporidium spp.; odontogenic infection related to infection by viridans streptococci; persistent cough related to infection by *Bordetella pertussis;* gas gangrene related to infection by *Clostridium perfringens* or Bacteroides spp.; and atherosclerosis related to infection by *Helicobacter pylori* or *Chlamydia pneumoniae.* Bacterial infections and protozoa infections and disorders related to such infections that may be treated or prevented in animals include the following: bovine respiratory disease related to infection by *P. haem., P. multocida, H. Somnus, Mycoplasma bovis,* or Bordetella spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae,* Klebsiella spp., Corynebacterium, or Enterococcus spp.; swine respiratory disease related to infection by *A. pleuro., P. muitocida,* or Mycoplasma spp.; swine enteric disease related to infection by *E. coli, Lawsonia intracellularis,* Salmonella, or *Serpulina hyodyisinteriae;* cow footrot related to infection by Fusobacterium spp.; cow metritis related to infection by *E. coli;* cow hairy warts related to infection by *Fusobacterium necrophorum* or *Bacteroides nodosus;* cow pink-eye related to infection by

*Moraxella bovis;* cow premature abortion related to infection by protozoa (i.e. neosporium); urinary tract infection in dogs and cats related to infection by *E. coli;* skin and soft tissue infections in dogs and cats related to infection by *Staph. epidermidis, Staph. intermedius, coagulase* neg. Staph. or *P. multocida;* and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. Said alkyl group may include one or two double or triple bonds. It is understood that for cyclic moieties at least three carbon atoms are required in said alkyl group.

The term "alkanoyl", as used herein, unless otherwise indicated, includes —C(O)-alkyl groups wherein "alkyl" is as defined above.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

As used herein, unless otherwise indicated, "Ac" indicates an acetyl group.

As used herein, unless otherwise indicated, "Me" indicates a methyl group.

As used herein, unless otherwise indicated, "Et" indicates an ethyl group.

As used herein, unless otherwise indicated, "Pr" indicates a propyl group.

As used herein, unless otherwise indicated, "Bt" indicates a butyl group.

The phrase "pharmaceutically acceptable salt(s)", as used herein, unless otherwise indicated, includes salts of acidic or basic groups which may be present in the compounds of formula I. The compounds of formula I that are basic in nature are capable of forming a wide variety of salts with various inorganic and organic acids. The acids that may be used to prepare pharmaceutically acceptable acid addition salts of such basic compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)]salts.

Hydroxy protecting groups can be prepared using methods known to those skilled in the art. For example, a hydroxy group can be protected by forming its silyl ethers, esters, carbonates, carbamates, borates, nitrates, and sulfenates, etc.

Those compounds of the formula I that are acidic in nature, are capable of forming base salts with various pharmacologically acceptable cations. Examples of such salts include the alkali metal or alkaline earth metal salts and particularly, the sodium and potassium salts.

The present invention also includes all radiolabelled forms of the compounds of formula I, and pharmaceutically acceptable salts thereof, wherein the radiolabel is selected from $^3$H, $^{11}$C and $^{14}$C. Such radiolabelled compounds are useful as research or diagnostic tools.

Certain compounds of formula I may have asymmetric centers and therefore exist in different enantiomeric forms. This invention relates to the use of all optical isomers and stereoisomers of the compounds of formula I and mixtures thereof. In particular, the invention includes all the stereoisomers at the 4" position of the cladinose. The compounds of formula I may also exist as tautomers. This invention relates to the use of all such tautomers and mixtures thereof.

DETAILED DESCRIPTION OF THE INVENTION

The preparation of the compounds of the present invention is illustrated in the following Schemes 1 to 6.

Scheme 1
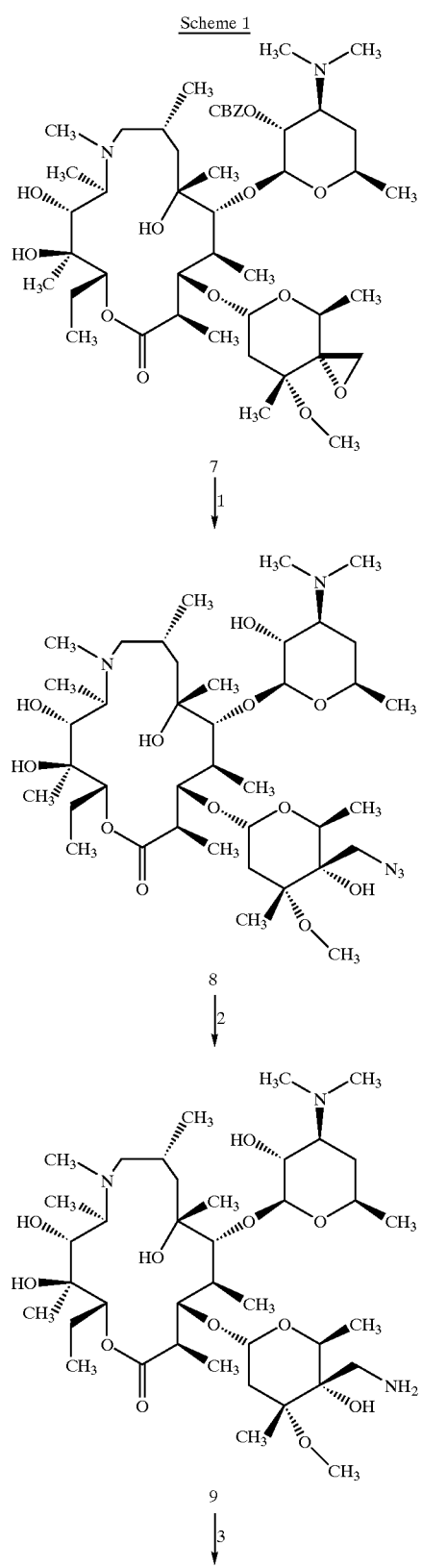
Scheme 2
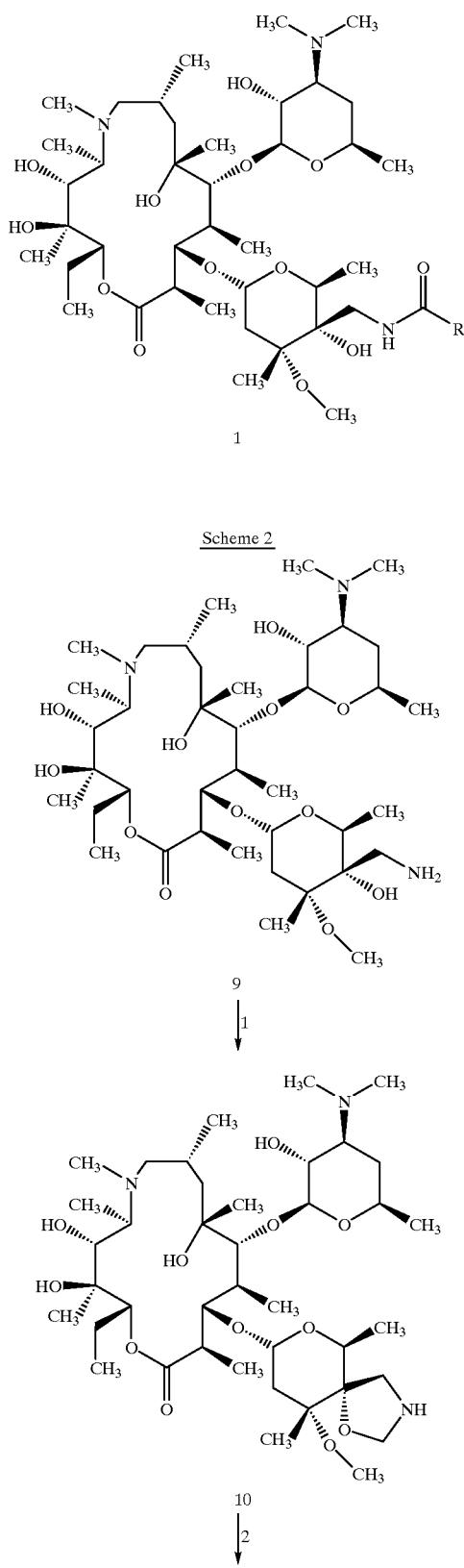

23
-continued
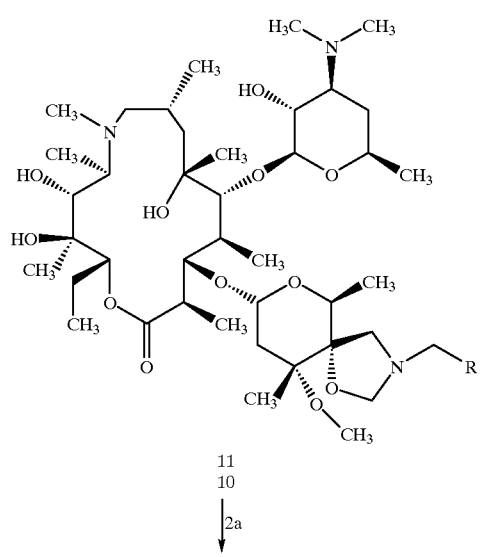
11
10
↓ 2a
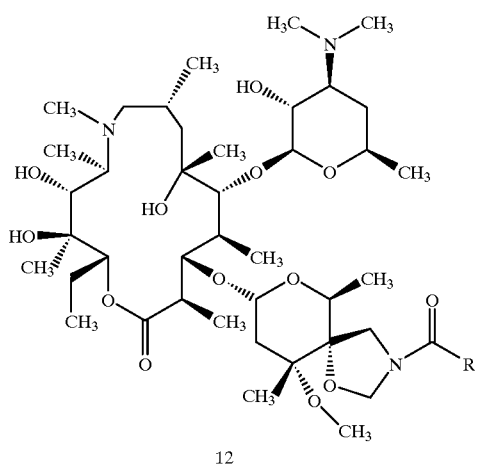
12
Scheme 3
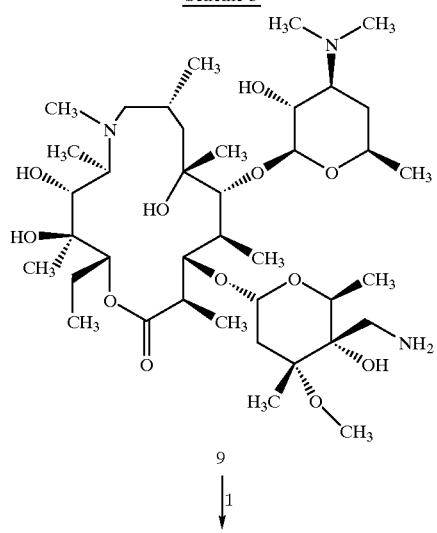
9
↓ 1
24
-continued
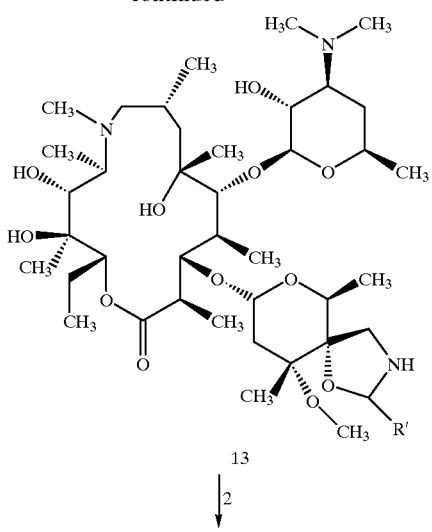
13
↓ 2
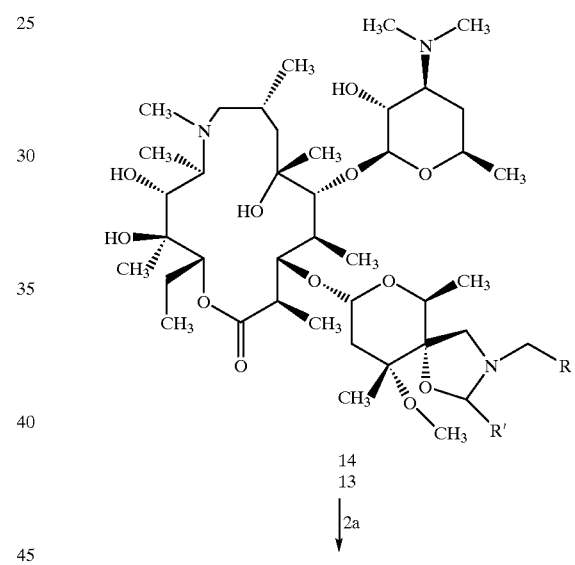
14
13
↓ 2a
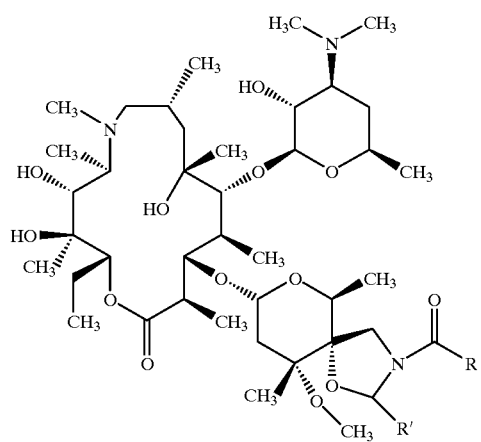
15

Scheme 4
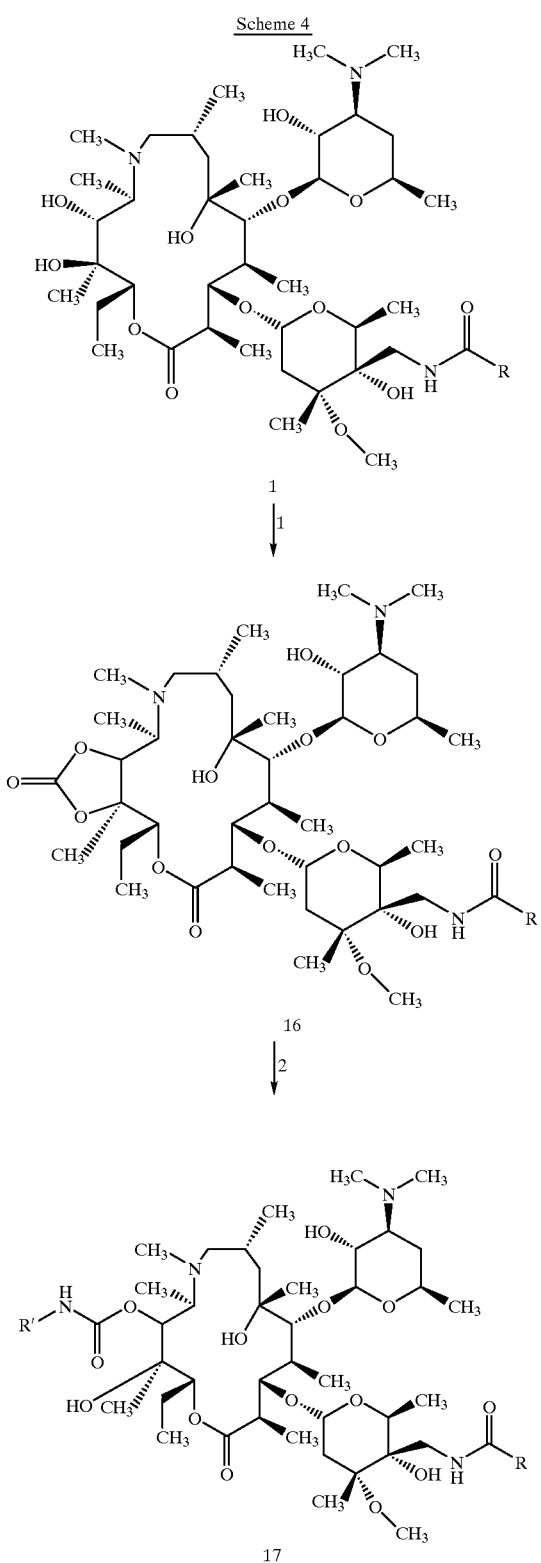
Scheme 5
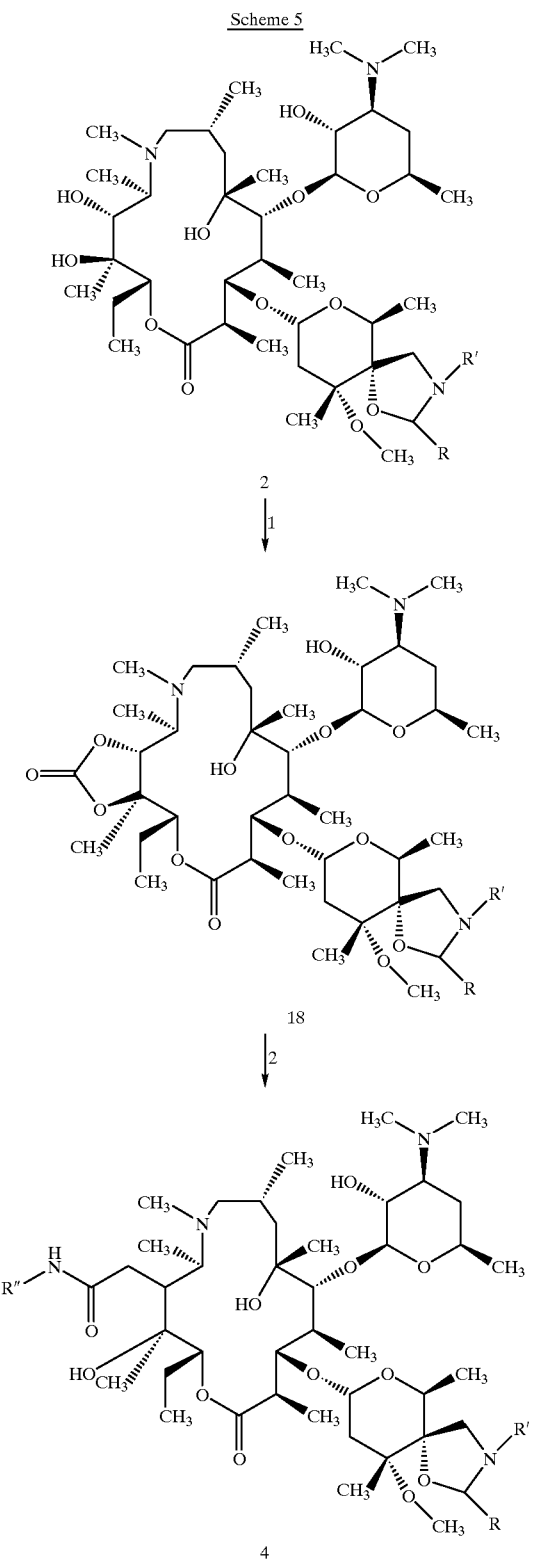

Scheme 6

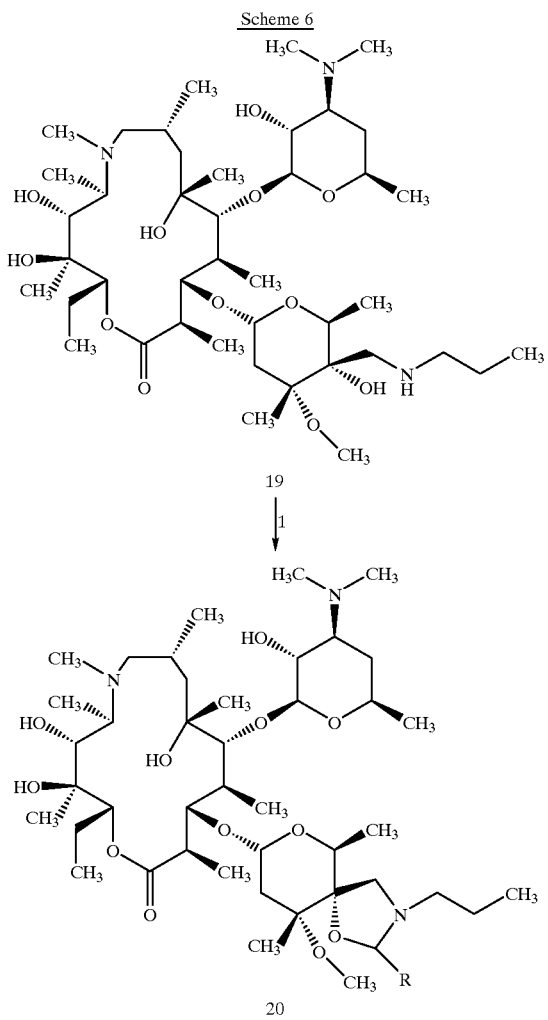

Scheme 1 illustrates the general synthesis of the compounds of formula 1 of the present invention. In Scheme 1, the starting compound 7 is prepared substantially as described in U.S. patent application Ser. No. 60/049348, filed Jun. 11, 1997, PCT/IB98/00839 (publication no. WO 98/56802), which is incorporated herein by reference in its entirety. In step 1 of Scheme 1, the 4"-epoxide of compound 7 was opened by sodium azide in the presence of ammonium chloride in methanol/water to generate the azide derivative of formula 8. In step 2 of Scheme 1, the azide functional group of formula 8 was converted to the corresponding amine of formula 9 by hydrogenation in ethyl acetate in the presence of 10% Pd on activated carbon. In step 3 of Scheme 1, the resultant amine of formula 9 was coupled with an acid employing EDC, HOBt, and $Et_3N$ in methylene chloride to give compound of formula 1.

Scheme 2 illustrates the general synthesis of the compounds of formula 12 of the present invention. In step 1 of Scheme 2, the compound of formula 9 was treated with formaldehyde in chloroform at 60° C. to generate the compound of formula 10. In step 2 of Scheme 2, the compound of formula 11 was prepared by reacting compound of formula 10 with an aldehyde, acetic acid and sodium triacetoxyborohydride in methylene chloride. In step 2a of Scheme 2, the compound of formula 12 was obtained by coupling the compound of formula 10 with an acid employing EDC, HOBt, and $Et_3N$ in methylene chloride.

Scheme 3 illustrates the general synthesis of the compounds of formulas 13, 14 and 15 of the present invention. In step 1 of Scheme 3, the compound of formula 13 is synthesized by treating the compound of formula 9 with an aldehyde in chloroform at an elevated temperature. In step 2 of Scheme 3, the compound of formula 13 is reacted with an aldehyde in the presence of acetic acid and sodium triacetoxyborohydride to give the compound of formula 14. In step 2a of Scheme 3, the compound of formula 13 is coupled with an acid to generate the compound of formula 15 employing EDC, HOBt, and $Et_3N$ in methylene chloride.

Scheme 4 illustrates the general synthesis of the compounds of formula 17 of the present invention. In step 1 of Scheme 4, the compound of formula 16 is prepared by treating the compound of formula 1 with ethylene carbonate, potassium carbonate in ethyl acetate at 75° C. In step 2 of Scheme 4, the compound of formula 17 is prepared by treating the compound of formula 16 with an amine.

Scheme 5 illustrates the general synthesis of the compounds of formula 4 of the present invention. In step 1 of Scheme 5, the compound of formula 18 is prepared by treating the compound of formula 2 with ethylene carbonate, potassium carbonate in ethyl acetate at 75° C. In step 2 of Scheme 5, the compound of formula 4 is synthesized by reacting the compound of formula 18 with an amine.

Scheme 6 illustrates the general synthesis of the compounds of formula 20 of the present invention. In step 1 of Scheme 6, the compound of formula 20 was prepared form the compound of formula 19 by reacting the compound of formula 19 with an aldehyde in chloroform at an elevated temperature.

Unless otherwise mentioned, all of the above steps in Schemes 1 to 6 were conducted at room temperature.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula I that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the formula I that are acidic in nature, are capable of forming base salts with various pharmacologically acceptable cations. Examples of such salts include the alkali metal or alkaline-earth metal salts and particularly, the sodium and potassium salts. These salts may be prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of the compounds of the present invention against bacterial and protozoa pathogens is demonstrated by the compound's ability to inhibit growth of defined strains of human (Assay I) or animal (Assays II to VII) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The antibacterial assay is performed in microtiter trays and interpreted according to *Performance Standards for Antimicrobial Disk Susceptibility Tests—Sixth Edition; Approved Standard,* published by The National Committee for Clinical Laboratory Standards (NCCLS) guidelines; the minimum inhibitory concentration (MIC) is used to compare strains. acr AB or acr AB-like indicates that an intrinsic multidrug efflux pump exists in the strain. Compounds are initially dissolved in dimethylsulfoxide (DMSO) as 40 mg/ml stock solutions.

| Strain Designation | Macrolide Resistance Mechanism(s) |
| --- | --- |
| Staphylococcus aureus 1116 | susceptible parent |
| Staphylococcus aureus 1117 | ermB |
| Staphylococcus aureus 0052 | susceptible parent |
| Staphylococcus aureus 1120 | ermC |
| Staphylococcus aureus 1032 | msrA, mph, esterase |
| Staphylococcus hemolyticus 1006 | msrA, mph |
| Streptococcus pyogenes 0203 | susceptible parent |
| Streptococcus pyogenes 1079 | ermB |
| Streptococcus pyogenes 1062 | susceptible parent |
| Streptococcus pyogenes 1061 | ermB |
| Streptococcus pyogenes 1064 | mefA |
| Streptococcus agalactiae 1024 | susceptible parent |
| Streptococcus agalactiae 1023 | ermB |
| Streptococcus pneumoniae 1016 | susceptible |
| Streptococcus pneumoniae 1046 | ermB |
| Streptococcus pneumoniae 1095 | ermB |
| Streptococcus pneumoniae 1175 | mefE |
| Haemophilus influenzae 0085 | susceptible; acr AB-like |
| Haemophilus influenzae 0131 | susceptible; acr AB-like |
| Moraxella catarrhalis 0040 | susceptible |
| Moraxella catarrhalis 1055 | erythromycin intermediate resistance |
| Escherichia coli 0266 | susceptible; acr AB |
| Haemophilus influenzae 1100 | susceptible; acr AB-like |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 $\mu$l of dimethylsulfoxide (DMSO). Dilutions of the test compound are prepared using uninoculated BHI broth. The concentrations of the test compound used range from 200 $\mu$g/ml to 0.098 $\mu$g/ml by twofold serial dilutions. The *P. multocida* inoculated BHI is diluted with uninoculated BHI broth to make a $10^4$ cell suspension per 200 $\mu$l. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 $\mu$l of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 $\mu$l of the *P. haemolytica* culture is inoculated onto BHI agar plates containing the various concentrations of the test compound using a Steers Replicator and incubated for 18 hours at 37° C. Initial concentrations of the test compound range from 100–200 μg/ml. The MIC is equal to the concentration of the test compound exhibiting 100% inhibition of growth of *P. haemolytica* as determined by comparison with an uninoculated control.

The in vivo activity of the compounds of formula (I) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3\times10^3$ CFU/ml bacterial suspension (*P. multocida* strain 59A006) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

Assay IV

The in vivo activity of the compounds of formula (I) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3\times10^3$ CFU/ml bacterial suspension (*P. multocida* strain 59A006) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

Assay V

Murine *Staphylococcus aureus* Intraperitoneal Infection Model

Mice (female CF-1) are allotted to cages (10 per cage) upon their arrival, and allowed to acclimate for a minimum of 48 hours before being used. Mice are infected intraperitoneally with 0.5 ml of a 3 to $5\times10^5$ colony forming units (CFU)/ml log phase culture of *Staphylococcus aureus* strain UC 6097 in 5% hog gastric mucin. Each experiment has one infected, non-medicated control group. Generally, all mice in a given study can be challenged within 30 to 90 minutes, especially if a repeating syringe (such as a Cornwall® syringe) is used to administer the challenge culture. Thirty minutes after infection has begun, compound treatment is given. It may be necessary for a second person to begin compound dosing if all of the animals have not been challenged at the end of thirty minutes. Subcutaneous doses are administered into the loose skin in the back of the neck whereas oral doses are given by means of a feeding needle. In both cases, a volume of 0.2 ml is used per mouse. A control compound of known efficacy administered by the same route is included in each test. Animals are observed daily, and the number of survivors in each group is recorded for 72 hours (three days) post challenge. The PD50 is a calculated dose at which the compound tested protects 50% of a group of mice from mortality due to the bacterial infection which would be lethal in the absence of drug treatment.

Assay VI

Murine *Staphylococcus aureus* Intramammary Infection Model

Lactating mice (female CF-1 that gave birth 2 to 5 days prior to the day of infection) (female CF-1) are allotted to cages (1 per cage) upon their arrival, and allowed to acclimate for 24–48 hours before being used. Mice are infected in the L4 mammary gland with 0.1 ml of a 300 to 450 colony forming units (CFU)/ml log phase culture of Staphylococcus aureus strain UC 6097. Each experiment has one infected, non-medicated control group. Thirty minutes after infection has begun, compound treatment is given. Subcutaneous doses are administered into the loose skin in the back of the neck whereas oral doses are given by means of a feeding needle. In both cases, a volume of 0.2 ml is used per mouse. The endpoint is the presence or absence of clinical mastitis symptoms and quantitation of bacterial numbers in the mammary glands five days after infection. Bacteria are quantitated by homogenizing the infected gland with 4 volumes of phosphate buffered saline for 30 seconds (Omni International, model TH). The homogenate and dilutions of the homogenate are plated on Brain Heart Infusion Agar, incubated at 37° C. overnight, and the colonies counted. The lower limit of detection is 50 CFU/gland. Infected, non-medicated mice have ~$5\times10^9$ CFU/gl and at the time of necropsy.

Assay VII
Determination Of MIC Of *Fusobacterium necrophorum* Isolated Using Anaerobic Plate Dilution Techniques Minimum inhibitory concentration (MIC) data may be collected from isolates of *Fusobacterium necrophorum* of cattle and sheep origin. The MIC values for *Fusobacterium necrophorum* are determined using plate dilution techniques and inoculation with a Steer's replicator. The procedures are those outlined in "Methods For Antimicrobial Susceptibility Testing Of Anaerobic Bacteria-Third Edition; Approved Standard" (vol. 13, no. 26, 1993) by the National Committee on Clinical Laboratory Standards (NCCLS). A total of 10 dilutions of the antimicrobials are tested as doubling dilutions of the drug (32 to 0.063 mcg/ml). Control strains of anaerobic bacteria (Clostridium perfringens ATCC 13124 and *Bacteroides fragilis* ATCC 25285) are used as controls on each inoculated plate.

The in vivo activity of the compounds of the present invention can be determined by conventional animal protection studies well known to those skilled in the art, usually carried out in rodents.

The compounds of formula I, and the pharmaceutically acceptable salts thereof (hereinafter "the active compounds"), may be administered through oral, parenteral, topical, or rectal routes in the treatment or prevention of bacterial or protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacr ylamide phenyl, polyhydroxyethylaspartamide-phenol, or polyethyleneoxide-polylysine substituted with palmitoylresidues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The Examples provided below illustrate specific embodiments of the invention, but the invention is not limited in scope to the Examples specifically exemplified.

EXAMPLE I

The compounds of examples 1 to 11 in Table 1 below have the formula 1 of Scheme

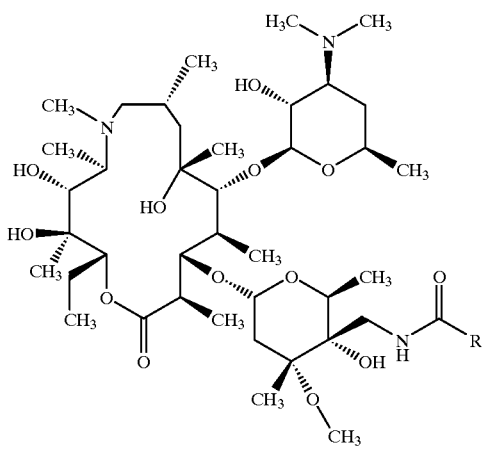

1 wherein the R substituents are as indicated in Table 1 below.

TABLE 1

Examples of Formula 1

| Example | RCO | MS | Yield |
|---|---|---|---|
| 1 | 3-pyridylcarbonyl | 883.2 | 53.5 |
| 2 | 2-furylcarbonyl | 872.1 | 47.1 |
| 3 | 3-quinolinylcarbonyl | 933.1 | 39.0 |
| 4 | 2-pyridylcarbonyl | 883.5 | 56.3 |
| 5 | 4-pyridylcarbonyl | 883.5 | 37.0 |
| 6 | 2-pyrazinylcarbonyl | 884.4 | 40.9 |
| 7 | 4-acetamidophenylcarbonyl | 939.5 | 46.0 |
| 8 | 2-pyrrolecarbonyl | 871.5 | 46.4 |
| 9 | 2-thiophenecarbonyl | 888.5 | 60.4 |
| 10 | cinnoline-4-carboxyl | 934.5 | 47.3 |
| 11 | 7,8-difluoro-3-quinolinylcarbonyl | 969.5 | 38.6 |

The compounds of formula 1 exemplified in Table 1 correspond to the compounds of formula I as follows:
$R^1$=H, $R^2$=$C_2H_5$, X=—$NR^4CH_2$—, $R^3$=H, $R^4$=$CH_3$, Z=—C(=O)$R^7$, where —C(=O)$R^7$ is exemplified by the RCO groups in Table 1, Q=H, and Y=H.

Preparation of 8

Azalide derivative 7 (20 g, 22.3 mmol), $NaN_3$ (7.26 g, 112 mmol), and $NH_4Cl$ (4.78 g, 89.4 mmol) were suspended in MeOH (40 mL) and water (20 mL). The reaction mixture was stirred at 65° C., the suspended material was dissolved in solution after 1 hour. The stirring was continued at 65° C. overnight, and the reaction was then quenched with saturated $NaHCO_3$ solution (250 mL). The aqueous layer was extracted with $CH_2Cl_2$ (3×250 mL), the combined organic layers were washed with brine (150 mL), and dried with $Na_2SO_4$. The solvent was removed in vacuo to give compound 8 in quantitative yield.

Preparation of 9

Azalide derivative 8 (17 g, 21.1 mmol) was dissolved in EtOAc (250 mL) in a parr flask, followed by the addition of 10% Pd/C (5.3 g) in EtOAc (250 mL). The mixture was hydrogenated at 45 PSI for 4 days. The catalyst was filtered off through celite, and the solvent was removed in vacuo to give compound 9 (10 g, 61%).

Preparation of 1

Azalide derivative 9 (250 mg, 0.321 mmol), EDC (77 mg, 0.402 mmol), HOBt (54 mg, 0.402 mmol) and carboxylic acid (0.643 mmol) were mixed and dried under vacuum for 20 minutes $CH_2Cl_2$ (2 mL) was then added, followed by the addition of $Et_3N$ (135 ml, 0.964 mmol). The reaction mixture was stirred at room temperature overnight. The reaction was diluted with $CH_2Cl_2$, then washed with saturated $NaHCO_3$ solution (2×60 mL) and brine (2×50 mL). The organic layer was dried ($Na_2SO_4$), and the solvent was removed in vacuo to give the crude product which was purified by flash chromatography using 9:1:1 of hexane:EtOAc:Diethylamine.

EXAMPLE II

The compounds of examples 1 to 3 in Table 2 below have the formula 12 of Scheme 2:

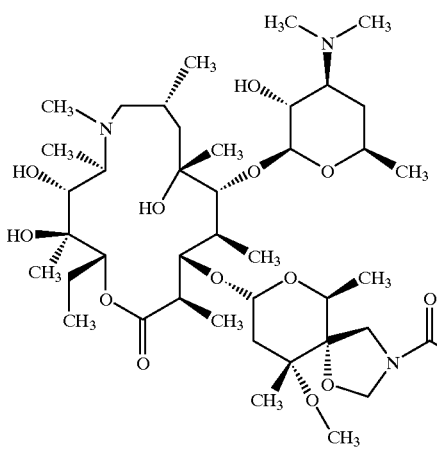

wherein the R substituents are as indicated in Table 2 below.

TABLE 2

Examples of Formula 12

| Examples | RCO | MS | Yield |
|---|---|---|---|
| 1 | 2-pyridylcarbonyl | 895.5 | 61.4 |
| 2 | 3-pyridylcarbonyl | 895.5 | 22.8 |
| 3 | 4-pyridylcarbonyl | 895.5 | 19.3 |

The compounds of formula 12 exemplified in Table 2 correspond to the compounds of formula II as follows:
$R^1$=H, $R^2$=$C_2H_5$, X=—$NR^4CH_2$—, $R^4$=$CH_3$, $R^{11}$=H, Q=H, W=—C(=O)$R^7$, where —C(O)$R^7$ is exemplified by the RCO groups of Table 2."

Preparation of 10

Azalide derivative 9 (1 g, 1.29 mmol) was dissolved in $CHCl_3$, followed by the addition of HCHO (107 mL, 3.856 mmol). The reaction mixture was stirred at 60° C. for 2 hours, and then cooled to room temperature. After diluted with $CH_2Cl_2$ (75 mL), the organic layer was washed with saturated $NaHCO_3$ solution (2×50 mL), brine (2×50 mL), and dried ($Na_2SO_4$). The solvent was removed in vacuo to give compound 10 (642 mg, 63%).

Preparation of 12

Azalide derivative 10 (100 mg, 0.127 mmol), EDC (30 mg, 0.158 mmol), HOBt (21 mg, 0.158 mmol) and carboxylic acid (0.253 mmol) were mixed and dried under vacuum for 20 minutes $CH_2Cl_2$ (1 mL) was then added, followed by the addition of Et₃N (38 ml, 0.38 mmol). The reaction mixture was stirred at room temperature overnight. The reaction was diluted with EtOAc (50 mL), then washed with saturated NaHCO₃ solution (2×60 mL) and brine (2×50 mL). The organic layer was dried (Na₂SO₄), and the solvent was removed in vacuo to give the crude product which was purified by flash chromatography using 5% MeOH/0.3% ammonia/CH₂Cl₂ to give the desired product.

What is claimed is:

1. A compound of the formula I

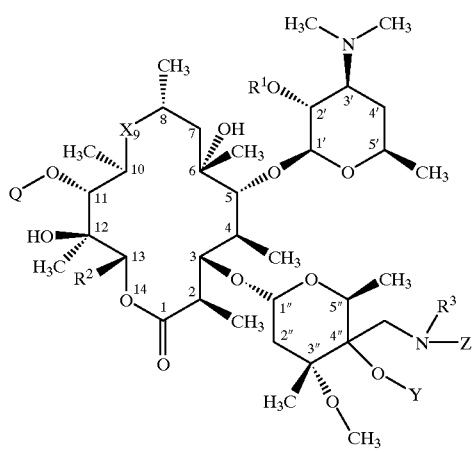

or a pharmaceutically acceptable salt thereof, wherein:

X is —CH₂NR⁴— or —NR⁴CH₂— wherein the first dash of each of the foregoing X groups is attached to the C-10 carbon of the compound of formula I and the last dash of each group is attached to the C-8 carbon of the compound of formula I;

Q is H or is a compound of the formula

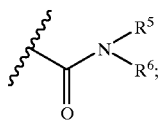

Y is H;

Z is —C(=O)R⁷, —S(=O)ₙR¹⁰, or —C(=O)OR¹⁰ wherein n is an integer ranging from 1 to 2;

R¹ is H or a hydroxy protecting group;

R² is an alpha-branched C₂–C₈ alkyl, alkenyl, alkynyl, alkoxyalkyl or alkylthioalkyl group, any of which may optionally be substituted by one or more hydroxyl groupsi a C₅–C₈ cycloalkylalkyl group wherein the alkyl group is an alpha-branched C₂–C₅ alkyl group, a C₃–C₈ cycloalkyl or a C₅–C₈ cycloalkenyl group, either of which may optionally be substituted by methyl or one or more hydroxyl groups or one or more C₁–C₄ alkyl groups or halo atoms, or a 3 to 6 membered oxygen or sulphur containing heterocyclic ring which may be saturated, or fully or partially unsaturated, and which may optionally be substituted by one or more C₁–C₄ alkyl groups or halo atoms;

or R² is phenyl, which may be optionally substituted with at least one substituent selected from C₁–C₄ the group consisting of alkyl, C₁–C₄ alkoxy and C₁–C₄ alkylthio groups, halogen atoms, hydroxyl groups, trifluoromethyl and cyano;

R³ is H, C₁–C₁₀ alkyl, C₂–C₁₀-alkenyl, C₂–C₁₀ alkynyl, —(CH₂)ₘ(C₆–C₁₀ aryl), or —(CH₂)ₘ(5–10 membered heteroaryl), wherein m is an integer ranging from 0 to 4, and wherein the alkyl, alkenyl, alkynyl, aryl and heteroaryl moieties of the foregoing R³ groups are optionally substituted by 1 to 3 substituents independently selected from the group consisting of halo, cyano, nitro, trifluoromethyl, azido, —C(O)R⁸, —OC(O)R⁸, —NR⁸C(O)R⁹, —C(O)NR⁸R⁹, —NR⁸R⁹, hydroxy, C₁–C₆ alkyl, C₁–C₆ alkoxy, C₆–C₁₀ aryl and a 5–10 membered heteroaryl;

R⁴ is H, C₁–C₁₀ alkyl, C₂–C₁₀ alkenyl, C₂–C₁₀ alkynyl, —(CH₂)ₘC₆–C₁₀aryl, or —(CH₂)ₘ(5–10 membered heteroaryl), wherein m is an integer ranging from 0 to 4, and wherein the alkyl, alkenyl, aryl, heteroaryl and alkynyl moieties of the foregoing R⁴ groups are optionally substituted by 1 to 3 substituents independently selected from the group consisting of halo, cyano, nitro, trifluoromethyl, azido, —C(O)R⁸, —OC(O)R⁸, —NR⁸C(O)R⁹, —C(O)NR⁸R⁹, —NR⁸R⁹, hydroxy, C₁–C₆ alkyl, C₁–C₆ alkoxy, C₆–C₁₀ aryl, and a 5–10 membered heteroaryl;

each R⁵ and R⁶ is independently H, C₁–C₁₀ alkyl, C₂–C₁₀ alkenyl, C₂–C₁₀ alkynyl, —(CH₂)ₘC₆–C₁₀ aryl, or —(CH₂)ₘ(5–10 membered heteroaryl), wherein m is an integer ranging from 0 to 4, and wherein the alkyl, alkenyl, aryl, heteroaryl and alkynyl moieties of the foregoing R⁵ and R⁶ groups are optionally substituted by 1 to 3 substituents independently selected from the group consisting of halo, cyano, nitro, trifluoromethyl, azido, —C(O)R⁸, —OC(O)R⁸, —NR⁸C(O)R⁹, —C(O)NR⁸R⁹, —NR⁸R⁹, hydroxy, C₁–C₆ alkyl, C₁–C₆ alkoxy, C₆–C₁₀ aryl, and a 5–10 membered heteroaryl;

or R⁵ and R⁶ may be taken together to form a 4–7 membered saturated ring or a 5–10 membered heteroaryl ring, wherein said saturated and heteroaryl rings optionally include 1 or 2 heteroatoms selected from the group consisting of O, S, and N, in addition to the nitrogen to which R⁵ and R⁶ are attached, wherein said saturated ring optionally includes 1 or 2 carbon-carbon double or triple bonds, and said saturated and heteroaryl rings are optionally substituted by 1 to 3 substituents independently selected from the group consisting of halo, cyano, nitro, trifluoromethyl, azido, —C(O)R⁸, —OC(O)R⁸, —NR⁸C(O)R⁹, —C(O)NR⁸R⁹, —NR⁸R⁹, hydroxy, C₁–C₆ alkyl, C₁–C₆ alkoxy, C₆–C₁₀ aryl, and a 5–10 membered heteroaryl;

R⁷ is C₁–C₁₀ alkyl, C₂–C₁₀ alkenyl, C₂–C₁₀ alkynyl, —CH₂OR⁸, —CH₂NR⁸R⁹, —(CH₂)ₘ(C₆–C₁₀ aryl), or —(CH₂)ₘ(5–10 membered heteroaryl), wherein m is an integer ranging from 0 to 4, and wherein the alkyl, alkenyl, alkynyl, aryl and heteroaryl moieties of the foregoing R⁷ groups are optionally substituted by 1 to 3 substituents independently selected from the group consisting of halo, cyano, nitro, trifluoromethyl, azido, —C(O)R⁸, —OC(O)R⁸, —NR⁸C(O)R⁹, —C(O)NR⁸R⁹, —NR⁸R⁹, hydroxy, C₁–C₆ alkyl, C₁–C₆ alkoxy, C₆–C₁₀ aryl, and a 5–10 membered heteroaryl;

each R⁸ and R⁹ is independently H, hydroxy, C₁–C₆ alkoxy, C₁–C₆ alkyl, C₂–C₆ alkenyl, (CH₂)ₘ(C₆–C₁₀ aryl), (CH₂)ₘ(5–10 membered heteroaryl), wherein m is an integer ranging from 0 to 4, or C₂–C₁₀ alkylyl;

R¹⁰ is C₁–C₁₀ alkyl, C₂–C₁₀ alkenyl, C₂–C₁₀ alkynyl, —(CH₂)ₘ(C₆–C₁₀ aryl), or —(CH₂)ₘ(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from the group consisting of halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

or $R^3$ is absent and Y and Z are taken together to form a heterocyclic ring of the formula

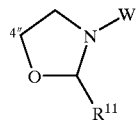

wherein W is H, —C(=O)$R^7$, —S(=O)$_n$$R^{10}$, —C(=O)OR$^{10}$, or —$CH_2R^7$ wherein n is an integer ranging from 1 to 2; and $R^{11}$ is H, $C_1$–$C_{10}$ alkyl, $C_2$–$C_{10}$ alkenyl, $C_2$–$C_{10}$ alkynyl, —(CH$_2$)$_m$$C_6$–$C_{10}$aryl, or —(CH$_2$)$_m$(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from the group consisting of halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl.

2. The compound of claim 1 wherein X is —$NR^4CH_2$—.

3. The compound of claim 2 wherein $R^4$ is H or $C_1$–$C_{10}$ alkyl.

4. The compound of claim 3 wherein $R^4$ is methyl, ethyl, propyl, butyl, cyclopropylmethyl, or cyclobutyl.

5. The compound of claim 1 wherein X is —$CH_2NR^4$—.

6. The compound of claim 5 wherein $R^4$ is H or $C_1$–$C_{10}$ alkyl.

7. The compound of claim 6 wherein $R^4$ is methyl, ethyl, propyl, butyl, cyclopropylmethyl, or cyclobutyl.

8. The compound of claim 1 wherein $R^3$ is H, $C_1$–$C_{10}$ alkyl, $C_2$–$C_{10}$-alkenyl, $C_2$–$C_{10}$ alkynyl, —(CH$_2$)$_m$($C_6$–$C_{10}$ aryl), or —(CH$_2$)$_m$(5–10 membered heteroaryl), wherein m is an integer ranging from 0 to 4, and wherein the alkyl, alkenyl, alkynyl, aryl and heteroaryl moieties of the foregoing $R^3$ groups are optionally substituted by 1 to 3 substituents independently selected from the group consisting of halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl and a 5–10 membered heteroaryl.

9. The compound of claim 8 wherein $R^3$ is H or $C_1$–$C_{10}$ alkyl.

10. The compound of claim 9 wherein $R^3$ is H.

11. The compound of claim 9 wherein $R^3$ is $CH_3$.

12. The compound of claim 1 wherein $R^3$ is absent and Y and Z are taken together to form a heterocyclic ring of the formula

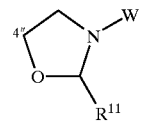

wherein W is H, —C(=O)$R^7$, —S(=O)$_n$$R^{10}$, —C(=O)OR$^{10}$, or —$CH_2R^7$ wherein n is an integer ranging from 1 to 2.

13. The compound of claim 12 wherein W is H.

14. The compound of claim 1 wherein Z is —C(=O)$R^7$.

15. The compound of claim 14 wherein $R^7$ is $C_1$–$C_{10}$ alkyl.

16. The compound of claim 1 wherein Z is —S(=O)$_n$$R^{10}$.

17. The compound of claim 16 wherein $R^{10}$ is $C_1$–$C_{10}$ alkyl.

18. The compound of claim 1 wherein Z is —C(=O)OR$^{10}$.

19. The compound of claim 18 wherein $R^{10}$ is $C_1$–$C_{10}$ alkyl.

20. The compound of claim 1 wherein Q is H.

21. The compound of claim 1 wherein Q is a compound of the formula

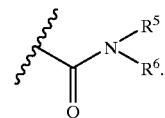

22. The compound of claim 21 wherein each $R^5$ and $R^6$ is independently H, $C_1$–$C_{10}$ alkyl, $C_2$–$C_{10}$ alkenyl, $C_2$–$C_{10}$ alkynyl, —(CH$_2$)$_m$$C_6$–$C_{10}$ aryl, or —(CH$_2$)$_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from the group consisting of halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl.

23. The compound of claim 21 wherein $R^5$ and $R^6$ may be taken together to form a 4–7 membered saturated ring or a 5–10 membered heteroaryl ring, wherein said saturated and heteroaryl rings optionally include 1 or 2 heteroatoms selected from the group consisting of O, S, and N, in addition to the nitrogen to which $R^5$ and $R^6$ are attached, wherein said saturated ring optionally includes 1 or 2 carbon-carbon double or triple bonds, and said saturated and heteroaryl rings are optionally substituted by 1 to 3 substituents independently selected from the group consisting of halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl.

24. The compound of claim 1 wherein $R^2$ is an alpha-branched $C_2$–$C_8$ alkyl, alkenyl, alkynyl, alkoxyalkyl or alkylthioalkyl group, any of which may optionally be substituted by one or more hydroxyl groups, a $C_5$–$C_8$ cycloalkylalkyl group wherein the alkyl group is an alpha-branched $C_2$–$C_5$ alkyl group, a $C_3$–$C_8$ cycloalkyl or a $C_5$–$C_8$ cycloalkenyl group, either of which may optionally be substituted by methyl or one or more hydroxyl groups or one or more $C_1$–$C_4$ alkyl groups or halo atoms, or a 3 to 6 membered oxygen or sulphur containing heterocyclic ring which may be saturated, or fully or partially unsaturated, and which may optionally be substituted by one or more $C_1$–$C_4$ alkyl groups or halo atoms.

25. The compound of claim 24 wherein $R^2$ is an alpha-branched $C_2$–$C_8$ alkyl.

26. The compound of claim 25 wherein $R^2$ is ethyl.

27. The compound of claim 1 wherein $R^2$ is phenyl, which may be optionally substituted with at least one substituent selected from the group consisting of $C_1$–$C_4$ alkyl, $C_1$–$C_4$ alkoxy and $C_1$–$C_4$ alkylthio groups, halogen atoms, hydroxyl groups, trifluoromethyl and cyano.

28. The compound of claim 1 wherein $R^1$ is H.

29. The compound of claim 1 wherein:

Q is H;

$R^1$ is H;

$R^2$ is ethyl;

$R^3$ is H or $C_1$–$C_{10}$ alkyl;

$R^4$ is H, methyl, ethyl, propyl, butyl, cyclopropylmethyl, or cyclobutyl;

Y is H;

$R^7$ is $C_1$–$C_{10}$ alkyl, $C_2$–$C_{10}$ alkenyl, $C_2$–$C_{10}$ alkynyl, —$CH_2OR^8$, —$CH_2NR^8R^9$, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

$R^{10}$ is $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl; and the pharmaceutically acceptable salts of the foregoing compounds.

30. The compound of claim 1 wherein:

Q is H;

$R^1$ is H;

$R^2$ is ethyl;

$R^4$ is H, methyl, ethyl, propyl, butyl, cyclopropylmethyl, or cyclobutyl; and $R^3$ is absent and Y and Z are taken together to form a heterocyclic ring of the formula

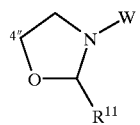

wherein $R^{11}$ is H and W is H, —$C(=O)R^7$, —$S(=O)_nR^{10}$, —$C(=O)OR^{10}$, or —$CH_2R^7$ wherein n is an integer ranging from 1 to 2;

$R^7$ is $C_1$–$C_{10}$ alkyl, $C_2$–$C_{10}$ alkenyl, $C_2$–$C_{10}$ alkynyl, —$CH_2OR^8$, —$CH_2NR^8R^9$, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

$R^{10}$ is $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl; or a pharmaceutically acceptable salt of the foregoing compound.

31. The compound of claim 1 wherein:

Q is a compound of the formula

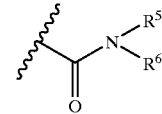

$R^1$ is H;

$R^2$ is ethyl;

$R^3$ is H or $C_1$–$C_{10}$ alkyl;

$R^4$ is H, methyl, ethyl, propyl, butyl, cyclopropylmethyl or cyclobutyl,

Y is H;

$R^5$ is H;

$R^6$ is $C_1$–$C_{10}$ alkyl, —$(CH_2)_mC_6$–$C_{10}$ aryl, or —$(CH_2)_m$(5–10 membered heteroaryl), wherein m is an integer ranging from 0 to 4, and wherein the alkyl, aryl, heteroaryl moieties of the foregoing $R^6$ group is optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$l aryl, and a 5–10 membered heteroaryl;

$R^7$ is $C_1$–$C_{10}$ alkyl, $C_2$–$C_{10}$ alkenyl, $C_2$–$C_{10}$ alkynyl, —$CH_2OR^8$, —$CH_2NR^8R^9$, $(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

$R^{10}$ is $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl; or a pharmaceutically acceptable salt of the foregoing compound.

32. The compound of claim 1 wherein:

Q is a compound of the formula:

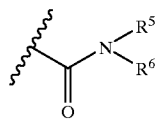

$R^1$ is H;

$R^2$ is ethyl;

$R^4$ is H, methyl, ethyl, propyl, butyl, cyclopropylmethyl, or cyclobutyl;

$R^5$ is H;

$R^6$ is $C_1-C_{10}$ alkyl, —$(CH_2)_m C_6-C_{10}$ aryl, or —$(CH_2)_m$ (5–10 membered heteroaryl), wherein m is an integer ranging from 0 to 4, and wherein the alkyl, aryl, heteroaryl moieties of the foregoing $R^6$ group is optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1-C_6$ alkyl, $C_1-C_6$ alkoxy, $C_6-C_{10}$ aryl, and a 5–10 membered heteroaryl;

and Y and Z are taken together to form a heterocyclic ring of the formula

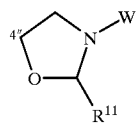

wherein $R^{11}$ is H and W is H, —$C(=O)R^7$, —$S(=O)_n R^{10}$, —$C(=O)OR^{10}$, or —$CH_2R^7$ wherein n is an integer ranging from 1 to 2;

$R^7$ is $C_1-C_{10}$ alkyl, $C_2-C_{10}$ alkenyl, $C_2-C_{10}$ alkynyl, —$CH_2OR^8$, —$CH_2NR^8R^9$, —$(CH_2)_m(C_6-C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1-C_6$ alkyl, $C_1-C_6$ alkoxy, $C_6-C_{10}$ aryl, and a 5–10 membered heteroaryl;

$R^{10}$ is $C_1-C_{10}$ alkyl, $C_2-C_{10}$ alkenyl, $C_2-C_{10}$ alkynyl, —$(CH_2)_m(C_6-C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1-C_6$ alkyl, $C_1-C_6$ alkoxy, $C_6-C_{10}$ aryl, and a 5–10 membered heteroaryl; or a pharmaceutically acceptable salt of the foregoing compound.

33. The compound of claim 1 wherein:

Q is H;

$R^1$ is H;

$R^2$ is Et;

$R^3$ is H;

X is —$NR^4CH_2$—;

$R^4$ is $CH_3$;

Y is H;

Z is —$C(=O)R^7$; and $R^7$ is selected from the group consisting of: 3-pyridyl, 2-furyl, 3-quinolinyl, 2-pyridyl, 4-pyridyl, 2-pyrazinyl, 4-acetamidophenyl, 2-pyrrole, 2-thiophene, 4-cinnolone and 7,8-difluoro-3-quinolinyl;

or a pharmaceutically acceptable salt of the foregoing compound.

34. The compound of claim 1 wherein:

Q is $R^6NHC(=O)$—;

$R^6$ is 3-pyridylmethyl;

$R^1$ is H;

$R^2$ is Et;

$R^3$ is H;

X is —$NR^4CH_2$—;

$R^4$ is $CH_3$;

Y is H;

Z is —$C(=O)R^7$; and $R^7$ is selected from the group consisting of: 3-pyridyl, 2-furyl, 3-quinolinyl, 2-pyridyl, 4-pyridyl, 2-pyrazinyl, 4-acetamidophenyl, 2-pyrrole, 2-thiophene, 4-cinnolone and 7,8-difluoro-3-quinolinyl;

or a pharmaceutically acceptable salt of the foregoing compound.

35. The compound of claim 1 wherein:

$R^3$ is absent and Y and Z are taken together to form a heterocyclic ring of the formula:

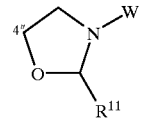

Q is H;

$R^1$ is H;

$R^2$ is Et;

X is —$NR^4CH_2$—;

$R^4$ is $CH_3$;

$R^{11}$ is H;

W is —$C(=O)R^7$;

$R^7$ is selected from the group consisting of: 3-pyridyl, 2-furyl, 3-quinolinyl, 2-pyridyl, 4-pyridyl, 2-pyrazinyl, 4-acetamidophenyl, 2-pyrrole, 2-thiophene, 4-cinnolone and 7,8-difluoro-3-quinolinyl;

or a pharmaceutically acceptable salt of the foregoing compound.

36. The compound of claim 1 wherein:

$R^3$ is absent and Y and Z are taken together to form a heterocyclic ring of the formula:

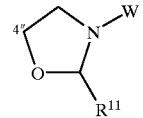

Q is H;

$R^1$ is H;

$R^2$ is Et;
X is —$NR^4CH_2$—;
$R^4$ is $CH_3$;
$R^{11}$ is H or Me;
W is ethyl, propyl, or butyl;
or a pharmaceutically acceptable salt of the foregoing compound.

37. The compound of claim 1 wherein:
$R^3$ is absent and Y and Z are taken together to form a heterocyclic ring of the formula:

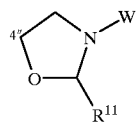

Q is $R^6NHC(=O)$—;
$R^6$ is 3-pyridylmethyl;
$R^1$ is H;
$R^2$ is Et;
X is —$NR^4CH_2$—;
$R^4$ is $CH_3$;
$R^{11}$ is H;
W is —$C(=O)R^7$;
$R^7$ is selected from the group consisting of: 3-pyridyl, 2-furyl, 3-quinolinyl, 2-pyridyl, 4-pyridyl, 2-pyrazinyl, 4-acetamidophenyl, 2-pyrrole, 2-thiophene, 4-cinnolone and 7,8-difluoro-3-quinolinyl;
or a pharmaceutically acceptable salt of the foregoing compound.

38. A pharmaceutical composition for the treatment of a bacterial or protozoa infection in a mammal, fish or bird which comprises a therapeutically effective amount of a compound of claim 1 and a pharmaceutically acceptable carrier.

39. A method of treating a bacterial or protozoa a infection in a mammal, fish, or bird which comprises administering to said mammal, fish, or bird a therapeutically effective amount of a compound of claim 1.

40. A compound of the formula II

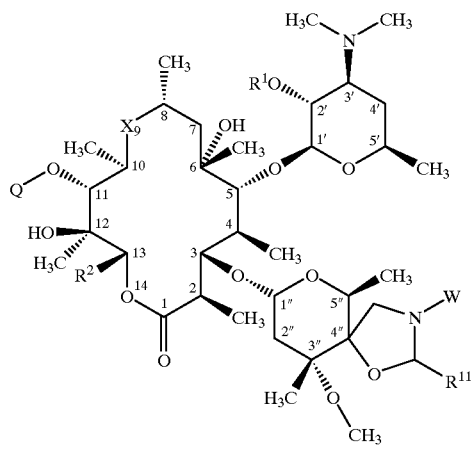

or a pharmaceutically acceptable salt thereof, wherein:
X is —$CH_2NR^4$— or —$NR^4CH_2$— wherein the first dash of each of the foregoing X groups is attached to C-10 carbon of the compound of formula II and the last dash of each group is attached to the C-8 carbon of the compound of formula II;
Q is H or is a compound of the formula

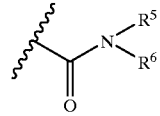

W is H, —$C(=O)R^7$, —$S(=O)_nR^{10}$, —$C(=O)OR^{10}$ or —$CH_2R^7$ wherein n is an integer ranging from 1 to 2;
$R^1$ is H or a hydroxy protecting group;
$R^2$ is an alpha-branched $C_2$–$C_8$ alkyl, alkenyl, alkynyl, alkoxyalkyl or alkylthioalkyl group any of which may optionally be substituted by one or more hydroxyl groups, a $C_5$–$C_8$ cycloalkylalkyl group wherein the alkyl group is an alpha-branched $C_2$–$C_5$ alkyl group, a $C_3$–$C_8$ cycloalkyl or $C_5$–$C_8$ cycloalkenyl group, either of which may optionally be substituted by methyl or one or more hydroxyl or one or more $C_1$–$C_4$ alkyl groups or halo atoms, or a 3 to 6 membered oxygen or sulphur containing heterocyclic ring which may be saturated, or fully or partially unsaturated and which may optionally be substituted by one or more $C_1$–$C_4$ alkyl groups or halo atoms;
or $R^2$ is phenyl which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl, and cyano;
$R^4$ is H, $C_1$–$C_{10}$ alkyl, $C_2$–$C_{10}$ alkenyl, $C_2$–$C_{10}$ alkynyl, —$(CH_2)_mC_6$–$C_{10}$ aryl, —$(CH_2)_m$(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$alkyl, $C_1$–$C_6$ alkoxy, $C_6$–$C_{10}$ aryl, and a 5–10 membered heteroaryl;
each $R^5$ and $R^6$ is independently H, $C_1$–$C_{10}$ alkyl, $C_2$–$C_{10}$ alkenyl, $C_2$–$C_{10}$ alkynyl, —$(CH_2)_mC_6$–$C_{10}$ aryl, or —$(CH_2)_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;
or $R^5$ and $R^6$ may be taken together to form a 4–7 membered saturated ring or a 5–10 membered heteroaryl ring, wherein said saturated and heteroaryl rings optionally include 1 or 2 heteroatoms selected from the group consisting of O, S, and N, in addition to the nitrogen to which $R^5$ and $R^6$ are attached, said saturated ring optionally includes 1 or 2 carbon-carbon double or triple bonds, and said saturated and heteroaryl rings are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

R⁷ is $C_1$–$C_{10}$ alkyl, $C_2$–$C_{10}$-alkenyl, $C_2$–$C_{10}$ alkynyl, —CH₂OR₈, —CH₂NR⁸R⁹, —(CH₂)$_m$($C_6$–$C_{10}$ aryl), or —(CH₂)$_m$(5–10 membered heteroaryl), wherein m is an integer ranging from 0 to 4, and wherein the alkyl, alkenyl, alkynyl, aryl and heteroaryl moieties of the foregoing R⁷ groups are optionally substituted by 1 to 3 substituents independently selected from the group consisting of halo, cyano, nitro, trifluoromethyl, azido, —C(O)R⁸, —OC(O)R⁸, —NR⁸C(O)R⁹, —C(O)NR⁸R⁹, —NR⁸R⁹, hydroxy, $C_1$–$C_6$ alkyl, $C_1$–$C_6$ alkoxy, $C_6$–$C_{10}$ aryl, and a 5–10 membered heteroaryl;

each R⁸ and R⁹ is independently H, hydroxy, $C_1$–$C_6$ alkoxy, $C_1$–$C_6$ alkyl, $C_2$–$C_6$ alkenyl, (CH₂)$_m$($C_6$–$C_{10}$ aryl), or (CH₂)$_m$(5–10 membered heteroaryl), wherein m is an integer ranging from 0 to 4, or $C_2$–$C_{10}$ alkylyl;

R¹⁰ is $C_1$–$C_{10}$ alkyl, $C_2$–$C_{10}$ alkenyl, $C_2$–$C_{10}$ alkynyl, —(CH₂)$_m$($C_6$–$C_{10}$ aryl), or —(CH₂)$_m$(5–10 membered heteroaryl), wherein m is an integer ranging from 0 to 4, and wherein the alkyl, alkenyl, alkynyl, aryl and heteroaryl moieties of the foregoing R¹⁰ groups are optionally substituted by 1 to 3 substituents independently selected from the group consisting of halo, cyano, nitro, trifluoromethyl, azido, —C(O)R⁸, —OC(O)R⁸, —NR⁸C(O)R⁹, —C(O)NR⁸R⁹, —NR⁸R⁹, hydroxy, $C_1$–$C_6$ alkyl, $C_1$–$C_6$ alkoxy, $C_6$–$C_{10}$ aryl, and a 5–10 membered heteroaryl; and R¹¹ is H, $C_1$–$C_{10}$ alkyl, $C_2$–$C_{10}$ alkenyl, $C_2$–$C_{10}$ alkynyl, —(CH₂)$_m$$C_6$–$C_{10}$aryl, or —(CH₂)$_m$(5–10 membered heteroaryl), wherein m is an integer ranging from 0 to 4, and wherein the alkyl, alkenyl, aryl, heteroaryl and alkynyl moieties of the foregoing R⁴ groups are optionally substituted by 1 to 3 substituents independently selected from the group consisting of halo, cyano, nitro, trifluoromethyl, azido, —C(O)R⁸, —OC(O)R⁸, —NR⁸C(O)R⁹, —C(O)NR⁸R⁹, —NR⁸R⁹, hydroxy, $C_1$–$C_6$ alkyl, $C_1$–$C_6$ alkoxy, $C_6$–$C_{10}$ aryl, and a 5–10 membered heteroaryl.

41. The compound of claim 40 wherein X is —NR⁴CH₂—.

42. The compound of claim 41 wherein R⁴ is H or $C_1$–$C_{10}$ alkyl.

43. The compound of claim 42 wherein R⁴ is methyl, ethyl, propyl, butyl, cyclopropylmethyl, or cyclobutyl.

44. The compound of claim 40 wherein X is —CH₂NR⁴—.

45. The compound of claim 44 wherein R⁴ is H or $C_1$–$C_{10}$ alkyl.

46. The compound of claim 45 wherein R⁴ is methyl, ethyl, propyl, butyl, cyclopropylmethyl, or cyclobutyl.

47. The compound of claim 40 wherein Q is H.

48. The compound of claim 40 wherein Q is a compound of the formula

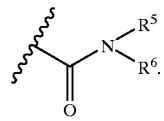

49. The compound of claim 48 wherein each R⁵ and R⁶ is independently H, $C_1$–$C_{10}$ alkyl, $C_2$–$C_{10}$ alkenyl, $C_2$–$C_{10}$ alkynyl, —(CH₂)$_m$$C_6$–$C_{10}$ aryl, or —(CH₂)$_m$(5–10 membered heteroaryl), wherein m is an integer ranging from 0 to 4, and wherein the alkyl, alkenyl, aryl, heteroaryl and alkynyl moieties of the foregoing R⁵ and R⁶ groups are optionally substituted by 1 to 3 substituents independently selected from the group consisting of halo, cyano, nitro, trifluoromethyl, azido, C(O)R⁸, —OC(O)R⁸, —NR⁸C(O)R⁹, —C(O)NR⁸R⁹, —NR⁸R⁹, hydroxy, $C_1$–$C_6$ alkyl, $C_1$–$C_6$ alkoxy, $C_6$–$C_{10}$ aryl, and a 5–10 membered heteroaryl.

50. The compound of claim 48 wherein R⁵ and R⁶ may be taken together to form a 4–7 membered saturated ring or a 5–10 membered heteroaryl ring, wherein said saturated and heteroaryl rings optionally include 1 or 2 heteroatoms selected from the group consisting of O, S, and N, in addition to the nitrogen to which R⁵ and R⁶ are attached, wherein said saturated ring optionally includes 1 or 2 carbon-carbon double or triple bonds, and said saturated and heteroaryl rings are optionally substituted by 1 to 3 substituents independently selected from the group consisting of halo, cyano, nitro, trifluoromethyl, azido, —C(O)R⁸, —OC(O)R⁸, —NR⁸C(O)R⁹, —C(O)NR⁸R⁹, —NR⁸R⁹, hydroxy, $C_1$–$C_6$ alkyl, $C_1$–$C_6$ alkoxy, $C_6$–$C_{10}$ aryl, and a 5–10 membered heteroaryl.

51. The compound of claim 40 wherein R² is an alpha-branched $C_2$–$C_8$ alkyl, alkenyl, alkynyl, alkoxyalkyl or alkylthioalkyl group, any of which may optionally be substituted by one or more hydroxyl groups, a $C_5$–$C_8$ cycloalkylalkyl group wherein the alkyl group is an alpha-branched $C_2$–$C_5$ alkyl group, a $C_3$–$C_8$ cycloalkyl or a $C_5$–$C_8$ cycloalkenyl group, either of which may optionally be substituted by methyl or one or more hydroxyl groups or one or more $C_1$–$C_4$ alkyl groups or halo atoms, or a 3 to 6 membered oxygen or sulphur containing heterocyclic ring which may be saturated, or fully or partially unsaturated, and which may optionally be substituted by one or more $C_1$–$C_4$ alkyl groups or halo atoms.

52. The compound of claim 51 wherein R² is an alpha-branched $C_2$–$C_8$ alkyl.

53. The compound of claim 52 wherein R² is ethyl.

54. The compound of claim 40 wherein R² is phenyl, which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl and cyano.

55. The compound of claim 40 wherein R¹ is H.

56. The compound of claim 40 wherein W is H.

57. The compound of claim 40 wherein:

Q is H;

R¹ is H;

R² is ethyl;

R⁴ is H, methyl, ethyl, propyl, butyl, cyclopropylmethyl, or cyclobutyl;

R¹¹ is H;

W is H, —C(=O)R⁷, —S(=O)$_n$R¹⁰, —C(=O)OR¹⁰, or —CH₂R⁷ wherein n is an integer ranging from 1 to 2;

R⁷ is $C_1$–$C_{10}$ alkyl, $C_2$–$C_{10}$ alkenyl, $C_2$–$C_{10}$ alkynyl, —CH₂OR⁸, —CH₂NR⁸R⁹, —(CH₂)$_m$($C_6$–$C_{10}$ aryl), or —(CH₂)$_m$(5–10 membered heteroaryl), wherein m is an integer ranging from 0 to 4, and wherein the alkyl, alkenyl, alkynyl, aryl and heteroaryl moieties of the foregoing R⁷ groups are optionally substituted by 1 to 3 substituents independently selected from the group consisting of halo, cyano, nitro, trifluoromethyl, azido, —C(O)R⁸, —OC(O)R⁸, —NR⁸C(O)R⁹, —C(O)NR⁸R⁹, —NR⁸R⁹, hydroxy, $C_1$–$C_6$ alkyl, $C_1$–$C_6$ alkoxy, $C_6$–$C_{10}$ aryl, and a 5–10 membered heteroaryl;

R¹⁰ is $C_1$–$C_{10}$ alkyl, $C_2$–$C_{10}$ alkenyl, $C_2$–$C_{10}$ alkynyl, —(CH₂)$_m$($C_6$–$C_{10}$ aryl), or —(CH₂)$_m$(5–10 membered heteroaryl), wherein m is an integer ranging from 0 to 4, and wherein the alkyl, alkenyl, alkynyl, aryl and heteroaryl moieties of the foregoing R¹⁰ groups are optionally substituted by 1 to 3 substituents independently selected from the group consisting of: halo, cyano, nitro, trifluoromethyl, azido, —C(O)R$^8$, —OC(O)R$^8$, —NR$^8$C(O)R$^9$, —C(O)NR$^8$R$^9$, —NR$^8$R$^9$, hydroxy, C$_1$–C$_6$ alkyl, C$_1$–C$_6$ alkoxy, C$_6$–C$_{10}$ aryl, and a 5–10 membered heteroaryl; or a pharmaceutically acceptable salts of the foregoing compounds.

58. The compound of claim 40 wherein Q is a compound of the formula:

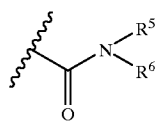

R$^1$ is H;

R$^2$ is ethyl;

R$^4$ is H, methyl, ethyl, propyl, butyl, cyclopropylmethyl, or cyclobutyl;

R$^5$ is H;

R$^6$ is C$_1$–C$_{10}$ alkyl, —(CH$_2$)$_m$C$_6$–C$_{10}$ aryl, or —(CH$_2$)$_m$(5–10 membered heteroaryl), wherein m is an integer ranging from 0 to 4, and wherein the alkyl, aryl, heteroaryl moieties of the foregoing R$^6$ group is optionally substituted by 1 to 3 substituents independently selected from the group consisting of halo, cyano, nitro, trifluoromethyl, azido, —C(O)R$^8$, —OC(O)R$^8$, —NR$^8$C(O)R$^9$, —C(O)NR$^8$R$^9$, —NR$^8$R$^9$, hydroxy, C$_1$–C$_6$ alkyl, C$_1$–C$_6$ alkoxy, C$_6$–C$_{10}$ aryl, and a 5–10 membered heteroaryl;

R$^{11}$ is H;

W is H, —C(=O)R$^7$, —S(=O)$_n$R$^{10}$, —C(=O)OR$^{10}$, or —CH$_2$R$^7$ wherein n is an integer ranging from 1 to 2;

R$^7$ is C$_1$–C$_{10}$ alkyl, C$_2$–C$_{10}$ alkenyl, C$_2$–C$_{10}$ alkynyl, —CH$_2$OR$^8$, —CH$_2$NR$^8$R$^9$, —(CH$_2$)$_m$(C$_6$–C$_{10}$ aryl), or —(CH$_2$)$_m$(5–10 membered heteroaryl), wherein m is an integer ranging from 0 to 4, and wherein the alkyl, alkenyl, alkynyl, aryl and heteroaryl moieties of the foregoing R$^7$ groups are optionally substituted by 1 to 3 substituents independently selected from the group consisting of halo, cyano, nitro, trifluoromethyl, azido, —C(O)R$^8$, —OC(O)R$^8$, —NR$^8$C(O)R$^9$, —C(O)NR$^8$R$^9$, —NR$^8$R$^9$, hydroxy, C$_1$–C$_6$ alkyl, C$_1$–C$_8$ alkoxy, C$_6$–C$_{10}$ aryl, and a 5–10 membered heteroaryl;

R$^{10}$ is C$_1$–C$_{10}$ alkyl, C$_2$–C$_{10}$ alkenyl, C$_2$–C$_{10}$ alkynyl, —(CH$_2$)$_m$(C$_6$–C$_{10}$ aryl), or —(CH$_2$)$_m$(5–10 membered heteroaryl), wherein m is an integer ranging from 0 to 4, and wherein the alkyl, alkenyl, alkynyl, aryl and heteroaryl moieties of the foregoing R$^{10}$ groups are optionally substituted by 1 to 3 substituents independently selected from the group consisting of halo, cyano, nitro, trifluoromethyl, azido, —C(O)R$^8$, —OC(O)R$^8$, —NR$^8$C(O)R$^9$, —C(O)NR$^{89}$, —NR$^8$R$^9$, hydroxy, C$_1$–C$_8$ alkyl, C$_1$–C$_6$ alkoxy, C$_6$–C$_{10}$ aryl, and a 5–10 membered heteroaryl; or a pharmaceutically acceptable salt of the foregoing compound.

59. The compound of claim 40 wherein:

Q is H;

R$^1$ is H;

R$^2$ is Et;

X is —NR$^4$CH$_2$—;

R$^4$ is CH$_3$;

R$^{11}$ is H;

W is —C(=O)R$^7$;

R$^7$ is selected from the group consisting of: 3-pyridyl, 2-furyl, 3-quinolinyl, 2-pyridyl, 4-pyridyl, 2-pyrazinyl, 4-acetamidophenyl, 2-pyrrole, 2-thiophene, 4-cinnolone and 7,8-difluoro-3-quinolinyl;

or a pharmaceutically acceptable salt of the foregoing compound.

60. The compound of claim 40 wherein:

Q is H;

R$^1$ is H;

R$^2$ is Et;

X is —NR$^4$CH$_2$—;

R$^4$ is CH$_3$;

R$^{11}$ is H or Me;

W is ethyl, propyl, or butyl;

or a pharmaceutically acceptable salt of the foregoing compound.

61. The compound of claim 40 wherein:

Q is R$^6$NHC(=O)—;

R$^6$ is 3-pyridylmethyl;

R$^1$ is H;

R$^2$ is Et;

X is —NR$^4$CH$_2$—;

R$^4$ is CH$_3$;

R$^{11}$ is H;

W is —C(=O)R$^7$;

R$^7$ is selected from the group consisting of: 3-pyridyl, 2-furyl, 3-quinolinyl, 2-pyridyl, 4-pyridyl, 2-pyrazinyl, 4-acetamidophenyl, 2-pyrrole, 2-thiophene, 4-cinnolone and 7,8-difluoro-3-quinolinyl;

or a pharmaceutically acceptable salt of the foregoing compound.

62. The compound of claim 40 wherein:

Q is H;

R$^1$ is H;

R$^2$ is Et;

X is —NR$^4$CH$_2$—;

R$^4$ is CH$_3$;

R$^{11}$ is H;

W is —C(=O)R$^7$;

R$^7$ is selected from the group consisting of: 3-pyridyl, 2-furyl, 3-quinolinyl, 2-pyridyl, 4-pyridyl, 2-pyrazinyl, 4-acetamidophenyl, 2-pyrrole, 2-thiophene, 4-cinnolone and 7,8-difluoro-3-quinolinyl;

or a pharmaceutically acceptable salt of the foregoing compound.

63. A pharmaceutical composition for the treatment of a bacterial or protozoa infection in a mammal, fish or bird which comprises a therapeutically effective amount of a compound of claim 40 and a pharmaceutically acceptable carrier.

64. A method of treating a bacterial or protozoa infection in a mammal, fish, or bird which comprises administering to said mammal, fish, or bird a therapeutically effective amount of a compound of claim 40.

65. A method of a method of preparing a compound of the formula I

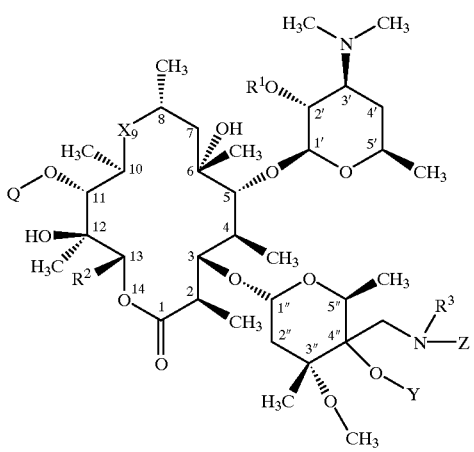

or a pharmaceutically acceptable salt thereof, wherein:
X is —$CH_2NR^4$— or —$NR^4CH_2$— wherein the first dash of each of the foregoing X groups is attached to the C-10 carbon of the compound of formula I and the last dash of each group is attached to the C-8 carbon of the compound of formula I;
Q is H or is a compound of the formula

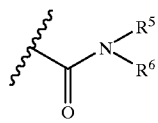

Y is H;
Z is —$C(=O)R^7$, —$S(=O)_nR^{10}$, or —$C(=O)OR^{10}$ wherein n is an integer ranging from 1 to 2;
$R^1$ is H or a hydroxy protecting group;
$R^2$ is an alpha-branched $C_2$–$C_8$ alkyl, alkenyl, alkynyl, alkoxyalkyl or alkylthioalkyl group, any of which may optionally be substituted by one or more hydroxyl groups, a $C_5$–$C_8$ cycloalkylalkyl group wherein the alkyl group is an alpha-branched $C_2$–$C_5$ alkyl group, a $C_3$–$C_8$ cycloalkyl or a $C_5$–$C_8$ cycloalkenyl group, either of which may optionally be substituted by methyl or one or more hydroxyl groups or one or more $C_1$–$C_4$ alkyl groups or halo atoms, or a 3 to 6 membered oxygen or sulphur containing heterocyclic ring which may be saturated, or fully or partially unsaturated, and which may optionally be substituted by one or more $C_1$–$C_4$ alkyl groups or halo atoms;
or $R^2$ is phenyl, which may be optionally substituted with at least one substituent selected from the group consisting of $C_1$–$C_4$ alkyl, $C_1$–$C_4$ alkoxy and $C_1$–$C_4$ alkylthio groups, halogen atoms, hydroxyl groups, trifluoromethyl and cyano;
$R^3$ is H, $C_1$–$C_{10}$ alkyl, $C_2$–$C_{10}$-alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^3$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl and a 5–10 membered heteroaryl;

$R^4$ is H, $C_1$–$C_{10}$ alkyl, $C_2$–$C_{10}$ alkenyl, $C_2$–$C_{10}$ alkynyl, —$(CH_2)_mC_6$–$C_{10}$aryl, or —$(CH_2)_m$(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;
each $R^5$ and $R^6$ is independently H, $C_1$–$C_{10}$ alkyl, $C_2$–$C_{10}$ alkenyl, $C_2$–$C_{10}$ alkynyl, —$(CH_2)_mC_6$–$C_{10}$ aryl, or —$(CH_2)_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;
or $R^5$ and $R^6$ may be taken together to form a 4–7 membered saturated ring or a 5–10 membered heteroaryl ring, wherein said saturated and heteroaryl rings optionally include 1 or 2 heteroatoms selected from the group consisting of O, S, and N, in addition to the nitrogen to which $R^5$ and $R^6$ are attached, wherein said saturated ring optionally includes 1 or 2 carbon-carbon double or triple bonds, and said saturated and heteroaryl rings are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;
$R^7$ is $C_1$–$C_{10}$ alkyl, $C_2$–$C_{10}$ alkenyl, $C_2$–$C_{10}$ alkynyl, —$CH_2OR^8$, —$CH_2NR^8R^9$, $(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from the group consisting of halo, cyano, nitro, trifluoromethyl, azido, —$C(O)R^8$, —$OC(O)R^8$, $NR^8C(O)R^9$, $C(O)NR^8R^9$, $NR^8R^9$, hydroxy, $C_1$–$C_6$ alkyl, $C_1$–$C_6$ alkoxy, $C_6$–$C_{10}$ aryl, and a 5–10 membered heteroaryl;
each $R^8$ and $R^9$ is independently H, hydroxy, $C_1$–$C_6$ alkoxy, $C_1$–$C_6$ alkyl, $C_2$–$C_6$ alkenyl, $(CH_2)_m(C_6$–$C_{10}$ aryl), $(CH_2)_m$(5–10 membered heteroaryl), wherein m is an integer ranging from 0 to 4, or $C_2$–$C_{10}$ alkylyl;
$R^{10}$ is $C_1$–$C_{10}$ alkyl, $C_2$–$C_{10}$ alkenyl, $C_2$–$C_{10}$ alkynyl, —$(CH_2)_m(C_6$–$C_{10}$ aryl), or —$(CH_2)_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from the group consisting of halo, cyano, nitro, trifluoromethyl, azido, —$C(O)R^8$, —$OC(O)R^8$, —$NR^8C(O)R^9$, —$C(O)NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;
or
$R^3$ is absent and Y and Z are taken together to form a heterocyclic ring of the formula

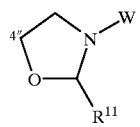

wherein W is H, —C(=O)R$^7$, —S(=O)$_n$R$^{10}$, —C(=O)OR$^{10}$, or —CH$_2$R$^7$ wherein n is an integer ranging from 1 to 2; and R$^{11}$ is H, C$_1$–C$_{10}$ alkyl, C$_2$–C$_{10}$ alkenyl, C$_2$–C$_{10}$ alkynyl, —(CH$_2$)$_m$C$_6$–C$_{10}$aryl, or —(CH$_2$)$_m$(5–10 membered heteroaryl), wherein m is an integer ranging from 0 to 4, and wherein the alkyl, alkenyl, aryl, heteroaryl and alkynyl moieties of the foregoing R$^4$ groups are optionally substituted by 1 to 3 substituents independently selected from the group consisting of halo, cyano, nitro, trifluoromethyl, azido, —C(O)R$^8$, —OC(O)R$^8$, —NR$^8$C(O)R$^9$, —C(O)NR$^8$R$^9$, —NR$^8$R$^9$, hydroxy, C$_1$–C$_6$ alkyl, C$_1$–C$_6$ alkoxy, C$_6$–C$_{10}$ aryl, and a 5–10 membered heteroaryl, which comprises treating a compound of the formula III

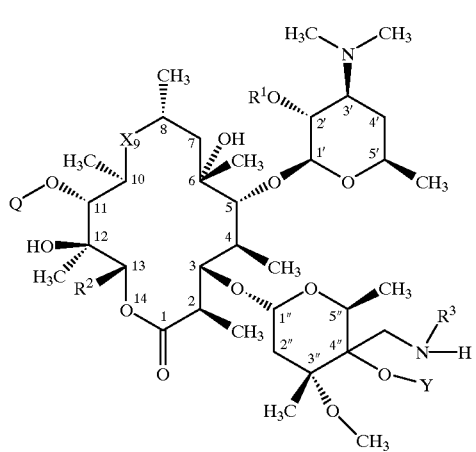

III wherein Q, X, Y, R$^1$, R$^2$, R$^3$, R$^4$, R$^5$, R$^6$, R$^8$ and R$^9$ are as defined for the compound of formula I, with a compound of the formula R$^7$C(=O)OH or R$^{10}$S(=O)$_n$OH in the presence of a coupling reagent, or R$^{10}$OC(=O)Cl wherein n, R$^7$, R$^{10}$ are as defined for the compound of formula I.

66. The method of claim 65 wherein the coupling reagent is EDC or HOBt.

67. A method of preparing a compound of the formula II

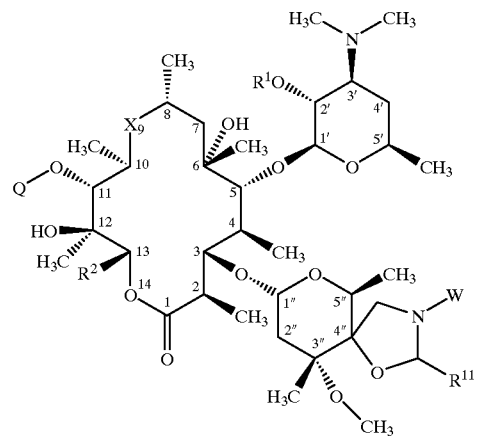

II or a pharmaceutically acceptable salt thereof, wherein:

X is —CH$_2$NR$^4$— or —NR$^4$CH$_2$— wherein the first dash of each of the foregoing X groups is attached to C-10 carbon of the compound of formula II and the last dash of each group is attached to the C-8 carbon of the compound of formula II;

Q is H or is a compound of the formula

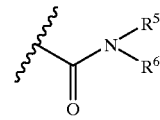

W is H, —C(=O)R$^7$, —S(=O)$_n$R$^{10}$, —C(=O)OR$^{10}$ or —CH$_2$R$^7$ wherein n is an integer ranging from 1 to 2;

R$^1$ is H or a hydroxy protecting group;

R$^2$ is an alpha-branched C$_2$–C$_8$ alkyl, alkenyl, alkynyl, alkoxyalkyl or alkylthioalkyl group any of which may optionally be substituted by one or more hydroxyl groups, a C$_5$–C$_8$ cycloalkylalkyl group wherein the alkyl group is an alpha-branched C$_2$–C$_5$ alkyl group, a C$_3$–C$_8$ cycloalkyl or C$_5$–C$_8$ cycloalkenyl group, either of which may optionally be substituted by methyl or one or more hydroxyl or one or more C$_1$–C$_4$ alkyl groups or halo atoms, or a 3 to 6 membered oxygen or sulphur containing heterocyclic ring which may be saturated, or fully or partially unsaturated and which may optionally be substituted by one or more C$_1$–C$_4$ alkyl groups or halo atoms;

or R$^2$ is phenyl which may be optionally substituted with at least one substituent selected from the group consisting of C$_1$–C$_4$ alkyl, C$_1$–C$_4$ alkoxy and C$_1$–C$_4$ alkylthio groups, halogen atoms, hydroxyl groups, trifluoromethyl, and cyano;

R$^4$ is H, C$_1$–C$_{10}$ alkyl, C$_2$–C$_{10}$ alkenyl, C$_2$–C$_{10}$ alkynyl, —(CH$_2$)$_m$C$_6$–C$_{10}$aryl, —(CH$_2$)$_m$(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from the group consisting of halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

each $R^5$ and $R^6$ is independently H, $C_1$–$C_{10}$ alkyl, $C_2$–$C_{10}$ alkenyl, $C_2$–$C_{10}$ alkynyl, —(CH$_2$)$_m$$C_6$–$C_{10}$ aryl, or —(CH$_2$)$_m$(5–10 membered heteroaryl), wherein m is an integer ranging from 0 to 4, and wherein the alkyl, alkenyl, aryl, heteroaryl and alkynyl moieties of the foregoing $R^5$ and $R^6$ groups are optionally substituted by 1 to 3 substituents independently selected from the group consisting of halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

or $R^5$ and $R^6$ may be taken together to form a 4–7 membered saturated ring or a 5–10 membered heteroaryl ring, wherein said saturated and heteroaryl rings optionally include 1 or 2 heteroatoms selected from the group consisting of O, S, and N, in addition to the nitrogen to which $R^5$ and $R^6$ are attached, said saturated ring optionally includes 1 or 2 carbon-carbon double or triple bonds, and said saturated and heteroaryl rings are optionally substituted by 1 to 3 substituents independently selected from the group consisting of halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

$R^7$ is $C_1$–$C_{10}$ alkyl, $C_2$–$C_{10}$-alkenyl, $C_2$–$C_{10}$ alkynyl, —CH$_2$O$R^8$, —CH$_2$N$R^8R^9$, —(CH$_2$)$_m$($C_6$–$C_{10}$ aryl), or —(CH$_2$)$_m$(5–10 membered heteroaryl), wherein m is an integer ranging from 0 to 4, and wherein the alkyl, alkenyl, alkynyl, aryl and heteroaryl moieties of the foregoing $R^7$ groups are optionally substituted by 1 to 3 substituents independently selected from the group consisting of halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl;

each $R^8$ and $R^9$ is independently H, hydroxy, $C_1$–$C_6$ alkoxy, $C_1$–$C_6$ alkyl, $C_2$–$C_6$ alkenyl, (CH$_2$)$_m$($C_6$–$C_{10}$ aryl), or (CH$_2$)$_m$(5–10 membered heteroaryl), wherein m is an integer ranging from 0 to 4, or $C_2$–$C_{10}$ alkylyl;

$R^{10}$ is $C_1$–$C_{10}$ alkyl, $C_2$–$C_{10}$ alkenyl, $C_2$–$C_{10}$ alkynyl, —(CH$_2$)$_m$($C_6$–$C_{10}$ aryl), or —(CH$_2$)$_m$(5–10 membered heteroaryl), wherein m is an integer ranging from 0 to 4, and wherein the alkyl, alkenyl, alkynyl, aryl and heteroaryl moieties of the foregoing $R^{10}$ groups are optionally substituted by 1 to 3 substituents independently selected from the group consisting of halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl; and $R^{11}$ is H, $C_1$–$C_{10}$ alkyl, $C_2$–$C_{10}$ alkenyl, $C_2$–$C_{10}$ alkynyl, —(CH$_2$)$_m$$C_6$–$C_{10}$aryl, or —(CH$_2$)$_m$(5–10 membered heteroaryl), wherein m is an integer ranging from 0 to 4, and wherein the alkyl, alkenyl, aryl, heteroaryl and alkynyl moieties of the foregoing $R^4$ groups are optionally substituted by 1 to 3 substituents independently selected from the group consisting of halo, cyano, nitro, trifluoromethyl, azido, —C(O)$R^8$, —OC(O)$R^8$, —$NR^8$C(O)$R^9$, —C(O)$NR^8R^9$, —$NR^8R^9$, hydroxy, $C_1$–$C_6$ alkyl, $C_1$–$C_6$ alkoxy, $C_6$–$C_{10}$ aryl, and a 5–10 membered heteroaryl, which comprises treating a compound of the formula IV

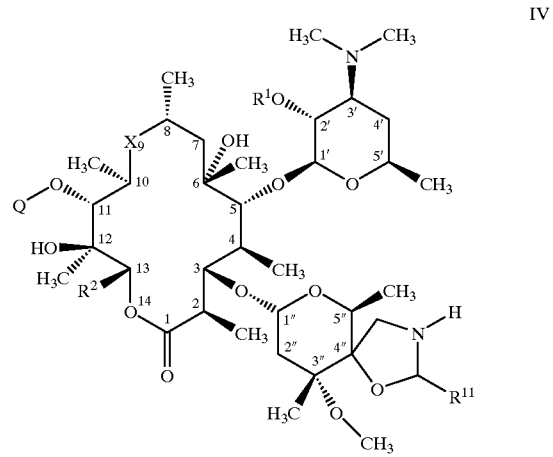

IV wherein Q, X, $R^1$, $R^2$, $R^4$, $R^5$, $R^6$, $R^8$, $R^9$, $R^{11}$ are as defined for the compound of formula II, with a compound of the formula $R^7$C(=O)OH, or $R^{10}$S(=O)$_n$OH in the presence of a coupling reagent, or $R^{10}$OC(=O)Cl, or $R^7$CHO in the presence of AcOH and NaB(OAc)$_3$H wherein n, $R^7$, $R^{10}$ are as defined in the compound of formula II.

68. The method of claim 67 wherein the coupling reagent is EDC or HOBt.

* * * * *